(12) United States Patent
Arfin et al.

(10) Patent No.: US 8,700,144 B2
(45) Date of Patent: Apr. 15, 2014

(54) ELECTRODE STIMULATOR WITH ENERGY RECYCLING AND CURRENT REGULATION

(75) Inventors: Scott K Arfin, Cambridge, MA (US); Rahul Sarpeshkar, Arlington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 243 days.

(21) Appl. No.: 13/096,670

(22) Filed: Apr. 28, 2011

(65) Prior Publication Data

US 2012/0277830 A1 Nov. 1, 2012

(51) Int. Cl.
*A61N 1/00* (2006.01)

(52) U.S. Cl.
USPC .......................................................... 607/2

(58) Field of Classification Search
USPC .................................... 607/2, 5, 62
See application file for complete search history.

(56) References Cited

U.S. PATENT DOCUMENTS

| | | | |
|---|---|---|---|
| 5,534,015 A * | 7/1996 | Kroll et al. | 607/7 |
| 5,602,497 A | 2/1997 | Thomas | |
| 6,415,181 B1 | 7/2002 | Schu et al. | |
| 6,426,628 B1 | 7/2002 | Palm et al. | |
| 6,968,231 B1 * | 11/2005 | Silvian et al. | 607/12 |
| 2003/0130699 A1 * | 7/2003 | Kelly et al. | 607/5 |
| 2005/0275382 A1 * | 12/2005 | Stessman et al. | 320/143 |

OTHER PUBLICATIONS

PCT International Search Report and Written Opinion, PCT/US2011/034351, Feb. 7, 2012.

* cited by examiner

*Primary Examiner* — Nicole F. Lavert
*Assistant Examiner* — Philip Edwards
(74) *Attorney, Agent, or Firm* — Quarles & Brady, LLP

(57) ABSTRACT

A system and method for stimulating an electrode is provided. The stimulator includes a sensor circuit configured to couple to the at least one electrode of a medical device to measure a power characteristic of the at least one electrode. The stimulator includes a control circuit configured to compare the measured power characteristic of the at least one electrode to a desired power characteristic, and, based upon a comparison of the measured power characteristic of the at least one electrode and the desired power characteristic, select between a first operational mode and a second operational mode of the electrode stimulator. The first operational mode includes delivering energy to the at least one electrode to stimulate the tissue and the second operational mode includes recovering energy from the at least one electrode.

10 Claims, 29 Drawing Sheets

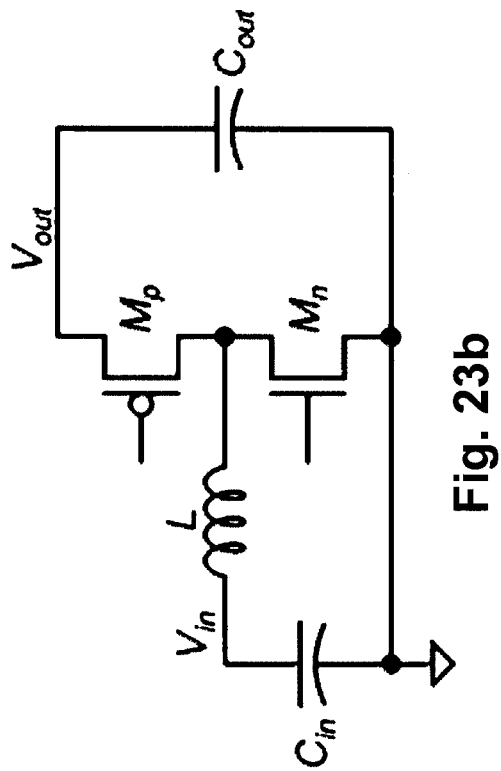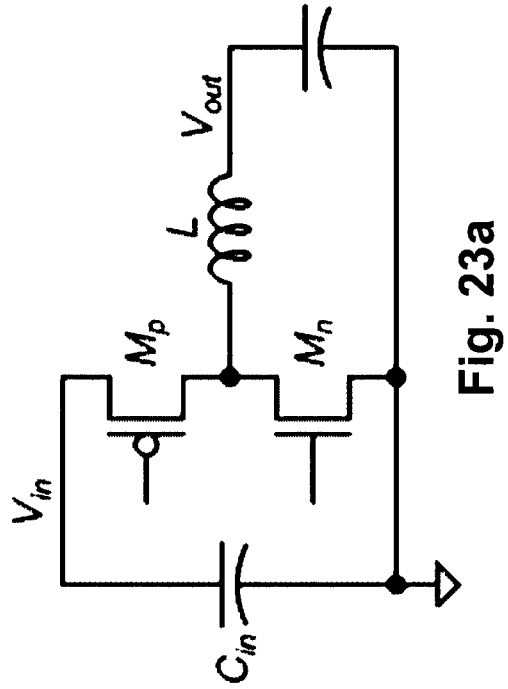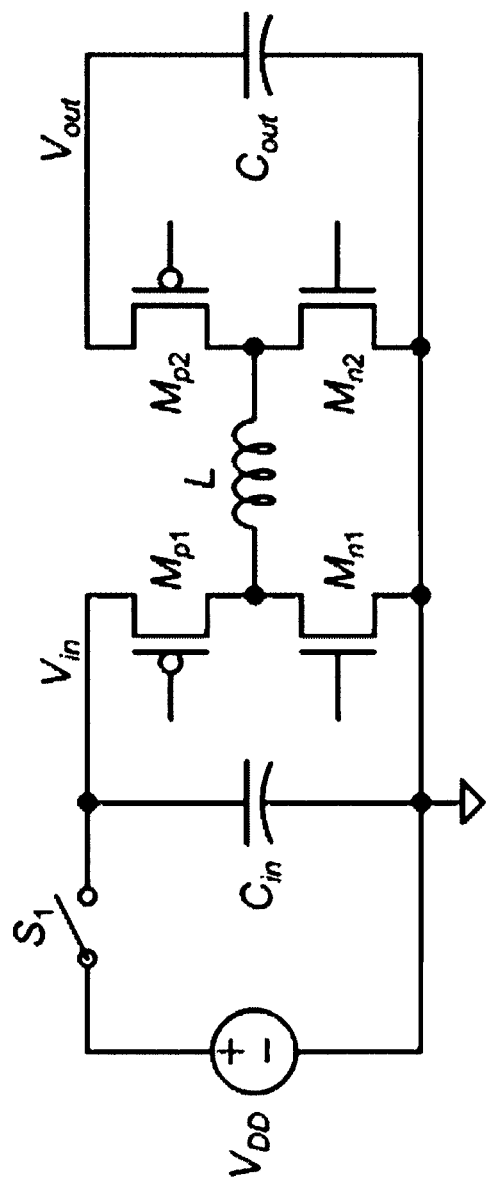
Fig. 23a
Fig. 23b
Fig. 23c

ELECTRODE STIMULATOR WITH ENERGY RECYCLING AND CURRENT REGULATION

STATEMENT REGARDING FEDERALLY SPONSORED RESEARCH

This invention was made with government support under N00014-09-1-1015 awarded by the Office of Naval Research and under NS056140 awarded by the National Institutes of Health. The government has certain rights in the invention.

FIELD OF THE INVENTION

The field of the invention is a system and method for the stimulation of tissue. More particularly, the invention relates to systems and methods for energy-efficient stimulation via an electrode stimulator using energy recycling and feedback current regulation.

BACKGROUND OF THE INVENTION

Electrical stimulation of tissues is an increasingly valuable tool for treating a variety of disorders. Electrical stimulators have many applications, such as cochlear implants for use in treating profound hearing loss, visual prostheses for treating blindness, spinal cord stimulators for treating severe chronic pain, muscle stimulators for treating paralysis, cardiac pacemakers for treating a variety of cardiac ailments, and deep brain stimulators for treating a number of neurological disorders. Deep brain stimulation, for example, can be used to treat tremor and Parkinson disease, and has also shown potential benefit for treating a variety of other disorders such as Tourette syndrome, pain, depression, and obsessive-compulsive disorder. Brain implants for paralysis treatments are increasingly providing sensory feedback via neural stimulation.

In the majority of implementations, clinicians make an effort to avoid the need to extend implantable electrical stimulators through the skin (for example, to connect the device to an external energy source) due to risk of infection. As such, these stimulators are often powered by an implanted battery or by an implanted RF coil receiving energy wirelessly. Thus, the energy efficiency of the stimulator is important in determining the size of the battery or coil and the lifetime of the device, and improvements in stimulator energy efficiency lead directly to reductions in battery or coil size, increases in battery lifetime, and reductions in tissue heating. Patient safety and comfort are increased, and medical costs are reduced if the size of the implant can be decreased.

In existing applications, current-source-based stimulators are generally favored because of their safety, established methods of charge balancing, and overall facility of implementation. But current-source stimulators are inefficient, consuming up to ten times the energy necessary to achieve stimulation of tissue. Voltage-based stimulators are sometimes used as an alternative to current stimulators due to their inherently higher energy efficiency. But voltage-based stimulators suffer from poor charge and current control and are sensitive to changes in electrode impedance.

Some stimulator systems have been developed that use a network of capacitors pre-charged to specific voltages as a power source for the electrode. The capacitors are connected directly to the electrode in sequence as a means of keeping the difference between the electrode voltage and capacitor voltage small, thus enabling improvements in energy efficiency. In those systems, though, currents are neither constant nor controlled.

Alternative systems have been developed that use added current limiters in series with the electrode to keep current through the electrode relatively constant. Because capacitor banks only allow for coarse discrete operation, though, both these implementations are inherently less energy efficient than continuous voltage-based implementations. The use of explicit current limiters in these implementations degrades energy efficiency.

SUMMARY OF THE INVENTION

The present invention overcomes the aforementioned drawbacks by providing a system and method for the stimulation of tissue. More particularly, the invention relates to systems and methods for energy-efficient stimulation via an electrode stimulator using energy recycling and feedback current regulation.

In one implementation, the present invention is a medical device configured to connect to a subject and deliver an electrical stimulation to tissue of the subject. The medical device includes a voltage power source, an electrode configured to deliver the electrical stimulation to the tissue of the subject, and a sensor circuit connected to the electrode and the voltage power source. The sensor circuit is configured to measure a power characteristic of the electrode. The device includes a control circuit connected to the voltage power source. The control circuit is configured to compare the measured power characteristic of the electrode to a desired power characteristic, and, based upon a comparison of the measured power characteristic of the electrode and the desired power characteristic, at least one of deliver energy to the electrode to stimulate the tissue and recover energy from the electrode. The control circuit is configured to operate in a stimulating down-conversion mode and a recycling up-conversion mode of operation.

In another implementation, the present invention is an electrode stimulator configured to connect to a medical device having at least one electrode configured to deliver an electrical stimulation to tissue of a subject having the medical device. The electrode stimulator includes a sensor circuit configured to be coupled to the at least one electrode of the medical device to measure a power characteristic of the at least one electrode, and a control circuit configured to compare the measured power characteristic of the at least one electrode to a desired power characteristic, and, based upon a comparison of the measured power characteristic of the at least one electrode and the desired power characteristic, select between a first operational mode and a second operational mode of the electrode stimulator. The first operational mode includes delivering energy to the at least one electrode to stimulate the tissue and the second operational mode includes recovering energy from the at least one electrode.

In another implementation, the present invention is an electrode stimulator configured to connect to a medical device having at least one electrode configured to deliver an electrical stimulation to tissue of a subject having the medical device. The electrode stimulator includes a current sensor circuit configured to measure a current flow through the at least one electrode, and define a set voltage by comparing the current flow through the at least one electrode to a desired current flow. The electrode stimulator includes a first stimulator core coupled to the at least one electrode and configured to at least one of deliver energy to the at least one electrode and recover energy from the at least one electrode based upon a comparison of a measured voltage across the at least one electrode and the set voltage.

In another implementation, the present invention is a method of stimulating an electrode configured to deliver an electrical stimulation to tissue of a subject having a medical device. The method includes measuring a current flow through the electrode, defining a set voltage by comparing the current flow through the electrode to a desired current flow, and measuring a voltage across the electrode. The method includes at least one of delivering energy to the electrode and recovering energy from the electrode based upon a comparison of the measured voltage across the electrode and the set voltage.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 6b is an illustration showing a preferable range of output voltages and flow of power for the adaptive voltage stimulator core shown in FIG. 6a.

FIG. 10 is a schematic diagram showing one example implementation of a DAC that may be used in implementing DAC and comparator of FIG. 5a.

FIGS. 23a-23c are schematic diagrams of two-mode adaptive voltage stimulators, and a four-mode adaptive voltage stimulator formed by combining two-mode adaptive voltage stimulators.

DETAILED DESCRIPTION OF THE INVENTION

The field of the invention is systems and methods for the stimulation of tissue. More particularly, the invention relates to a system and method for energy-efficient stimulation via an electrode stimulator using inductive energy recycling and feedback current regulation.

To the accomplishment of the foregoing and related ends, the disclosure, then, comprises the features hereinafter fully described. The following description and the annexed drawings set forth in detail certain illustrative aspects of the disclosure. However, these aspects are indicative of but a few of the various ways in which the principles of the disclosure can be employed. Other aspects, advantages and novel features of the disclosure will become apparent from the following detailed description of the disclosure when considered in conjunction with the drawings.

The various aspects of the subject disclosure are now described with reference to the annexed drawings, wherein like numerals refer to like or corresponding elements throughout. It should be understood, however, that the drawings and detailed description relating thereto are not intended to limit the claimed subject matter to the particular form disclosed. Rather, the intention is to cover all modifications, equivalents, and alternatives falling within the scope of the claimed subject matter.

Figure 5A:
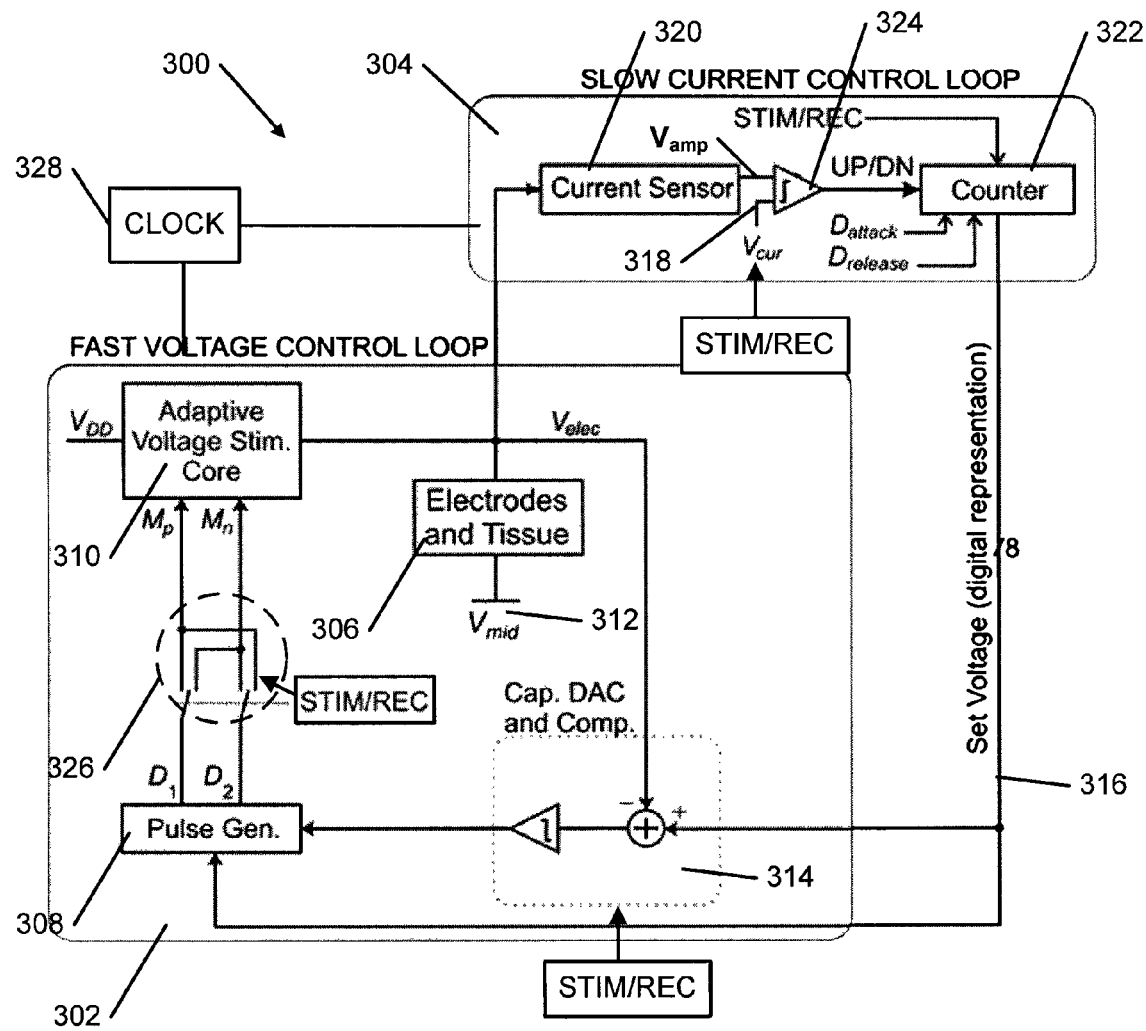
FIG. 5a is a block diagram showing additional detail of the functional components of an electrode stimulator configured in accordance with the present disclosure including two feedback loops for controlling the adaptive voltage stimulator.
Figure 5B:
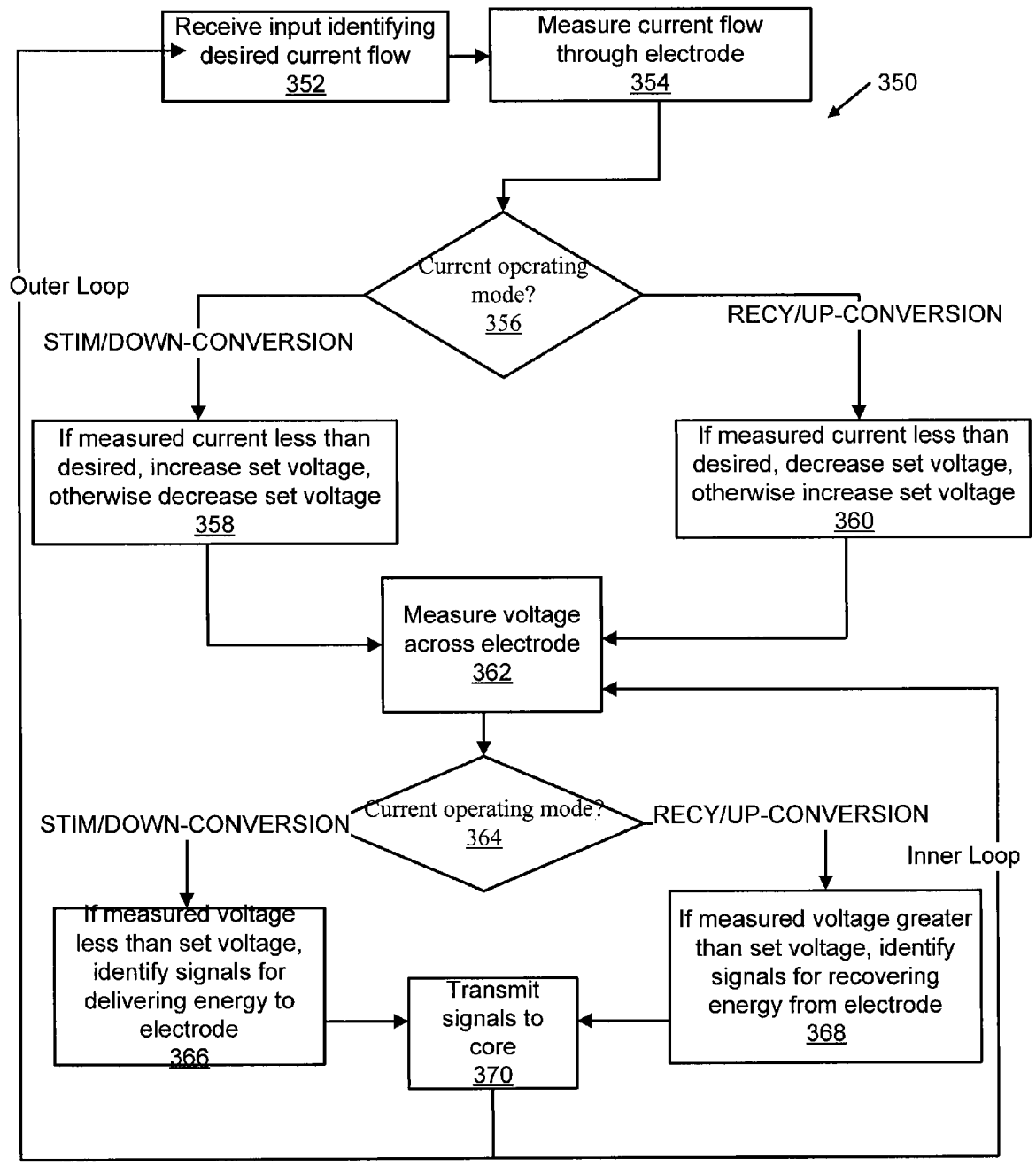
FIG. 5b is a flow chart illustrating a sequence of steps that may be executed by an electrode stimulator to stimulate an electrode using inductive energy recycling and feedback current regulation.

The schematic flow chart diagrams included in the present disclosure are generally set forth as logical flow-chart diagrams (e.g., FIG. 5b). As such, the depicted order and labeled steps are indicative of one embodiment of the presented method. Other steps and methods may be implemented that are equivalent in function, logic, or effect to one or more steps, or portions thereof, of the illustrated method. Additionally, the format and symbols employed are provided to explain the logical steps of the method and do not limit the scope of the method. Additionally, the order in which particular steps of the present method occur may or may not strictly adhere to the order of the corresponding steps shown.

The present system provides an energy-efficient electrode stimulator configured to use inductive storage and recycling of energy in an adaptive voltage stimulator. The system drives an electrode in an approximately adiabatic fashion to control energy consumption. In the present disclosure, adiabatic operation refers to a mode of operation where a voltage applied to the electrode at a first time is approximately equal to the voltage of the electrode at the same time. This operation controls energy losses in both the electrode and the circuitry driving the electrode. The present system may also incorporate a shunt current sensor to monitor and regulate current through the electrode. The shunt current sensor incorporates a feedback control loop to enable flexible and safe stimulation.

The present adaptive voltage stimulator, therefore, allows for efficient transfer of energy both to and from an electrode and can be based on a direct current-direct current (DC-DC) converter topology. The stimulator can be operated in a bidirectional fashion in two different operational modes—a stimulating down-conversion mode and a recycling up-conversion mode. Stimulating down-conversion refers to a power transfer mode in which the direction of current flow is from an energy source into an electrode, where the voltage of the electrode is less than the voltage of the energy source. A recycling up-conversion mode refers to a power transfer mode in which the direction of current flow is from an electrode into an energy source, where the voltage of the electrode is greater than the voltage of the energy source.

The present system, therefore, combines the efficiency of voltage control and the safety and accuracy of current control into a single electrode stimulator system. The stimulator or portions thereof may be implemented, for example, via a standard 0.35 micrometer CMOS process, or any other suitable semiconductor fabrication process.

Although the present electrode stimulator system has many applications, example uses include neural, cardiac, retinal, cochlear, muscular, and other biomedical implants where low power operation is important. In various applications, the stimulator can be incorporated into implantable medical devices. Alternatively, the stimulator can be used in devices that make up functional components of a body sensor network.

Figure 1:
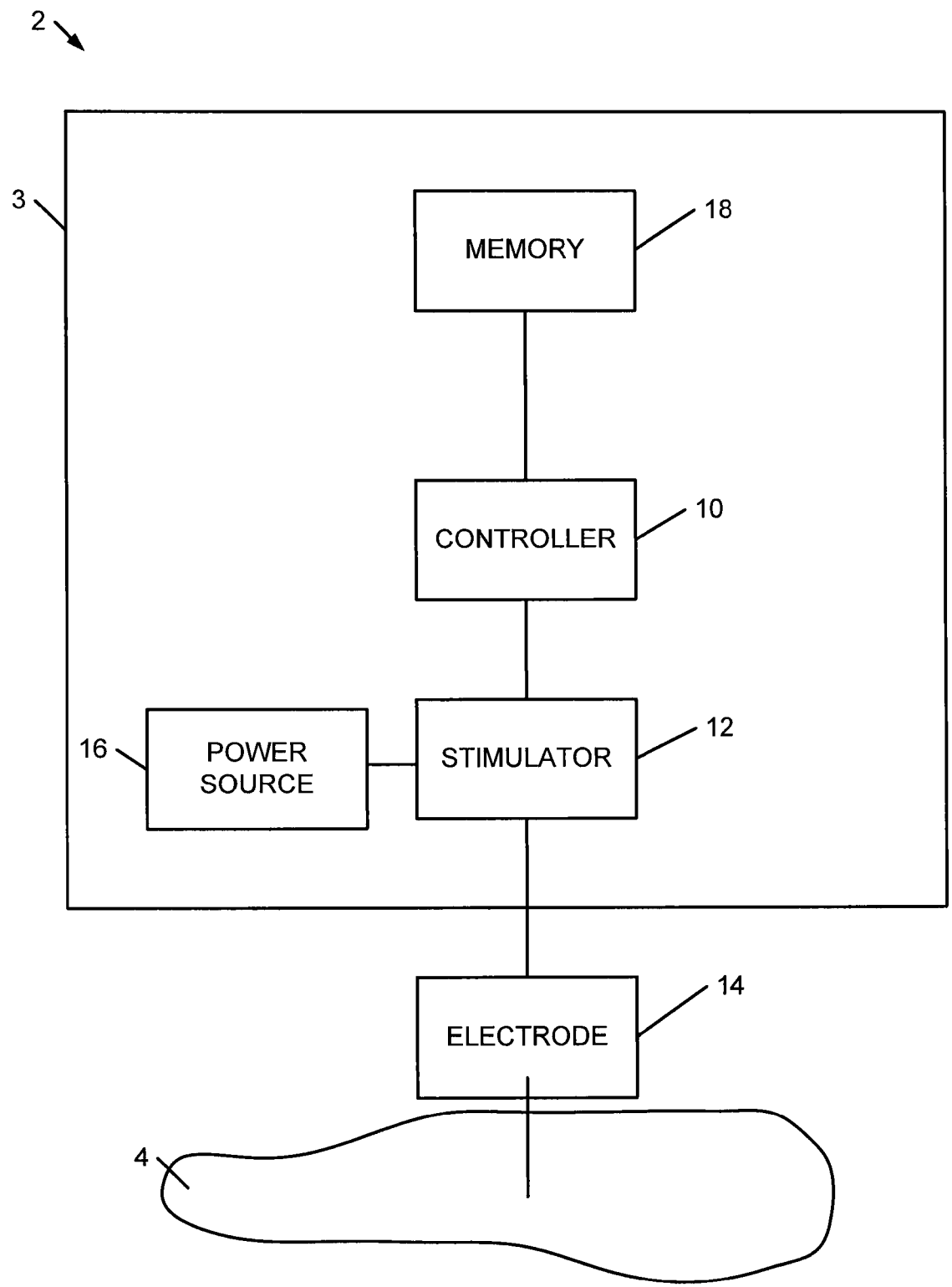
FIG. 1 is a block diagram illustrating the functional components of an example biomedical implant in accordance with the present disclosure.

FIG. 1 is a block diagram of the functional components of an example biomedical or medical implant 2 incorporating the present electrode stimulator and configured to interface with an associated tissue 4. Implant 2 includes housing 3 that is constructed from a biocompatible material for housing controller 10, stimulator 12, and electrode 14. Controller 10 is configured to implement an algorithm stored in memory 18 to treat a condition within a patient by causing an electrical signal to be applied to electrode 14. Electrode 14 then communicates that energy to tissue 4. In various applications, depending upon the location of medical implant 2 and the type of tissue 4 in which electrode 14 is situated or to which electrode 14 is attached or near to, the energy can be delivered via cochlear implants for use in treating profound hearing loss, visual prostheses for treating blindness, spinal cord stimulators for treating severe chronic pain, muscle stimulators for treating paralysis, cardiac pacemakers for treating a variety of cardiac ailments, or deep brain stimulators for treating a number of neurological disorders, for example.

Controller 10 controls energy delivery to electrode 14 by supplying an input signal to stimulator 12. The input signal describes a characteristic (e.g., voltage or current magnitude) of an electrical signal that is to be delivered to electrode 14 by stimulator 12. Stimulator 12 uses the input from controller 10, in combination with power source 16, to modify and control an electrical signal that is delivered to electrode 14 to meet the requirements of the input signal received from controller 10. As will be described in detail and with further context, for example, with reference to FIG. 5a, in one implementation the desired signal is established the $V_{cur}$ input of comparator 324.

Stimulator 12 of the present disclosure generally has two operational modes—stimulating down-conversion and recycling up-conversion. Stimulator 12 may be put into either of these modes of operation by controller 10, or another controller either connected to, or incorporated into stimulator 12.

Figures 2A, 2B:
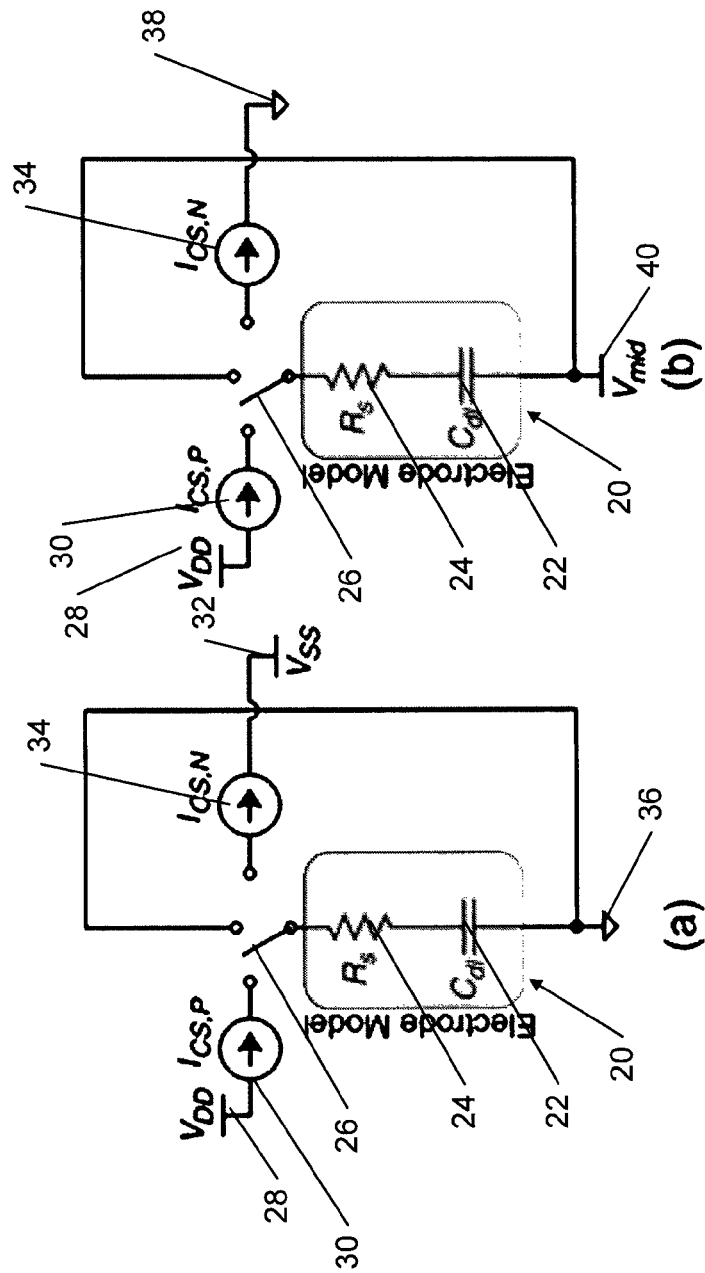
FIGS. 2a and 2b are schematic diagrams of prior-art electrode stimulators that use current-source-based power supplies to drive a connected electrode.

Many existing electrode stimulator systems use current source-based power sources due to their relatively precise, safe controllability. These power sources, though, can be quite inefficient. FIGS. 2a and 2b illustrate electrode stimulators that use current-source-based power supplies to drive a connected electrode. In each figure, electrode 20 is modeled as a series connection of resistor 24 ($R_s$) and capacitor 22 ($C_{dl}$). The electrode can be modeled using, for example, the model described in J. E. B. Randles. Kinetics of rapid electrode reactions. *Disc Faraday Soc,* 1:11-19, 1947. As such, the parameter $R_S$ is the solution resistance, and $C_{dl}$ is the double-layer capacitance. Ideal electrodes have minimal series resistance and high capacitance, enabling effective operation at lower voltages.

In FIG. 2a, switch 26 allows electrode 20 to be connected to either of positive power supply 28 ($V_{DD}$) via current source 30 ($I_{CS,P}$), negative power supply 32 ($V_{SS}$) via current source 34 ($I_{CS,N}$) or ground 36 to short out any accumulated charge. Both current sources 30 and 34 restrict the flow of current, dissipating a large amount of energy due to the voltage difference between the power supply and the electrode appearing across the current sources.

FIG. 2b shows a similar circuit as that shown in FIG. 2a, but voltages have been shifted such that electrode 20 can now be connected to either power supply 28 ($V_{DD}$) or ground 38 via current source 34, while the electrode baseline potential is set midway by a second supply 40 ($V_{mid}$). To keep the circuits of FIGS. 2a and 2b balanced, for this disclosure, $V_{DD}$ of FIG. 2b is set equal to $V_{DD}+V_{SS}$ of FIG. 2a, with $V_{mid}$ halfway between $V_{DD}$ of FIG. 2b and ground.

Figure 3:
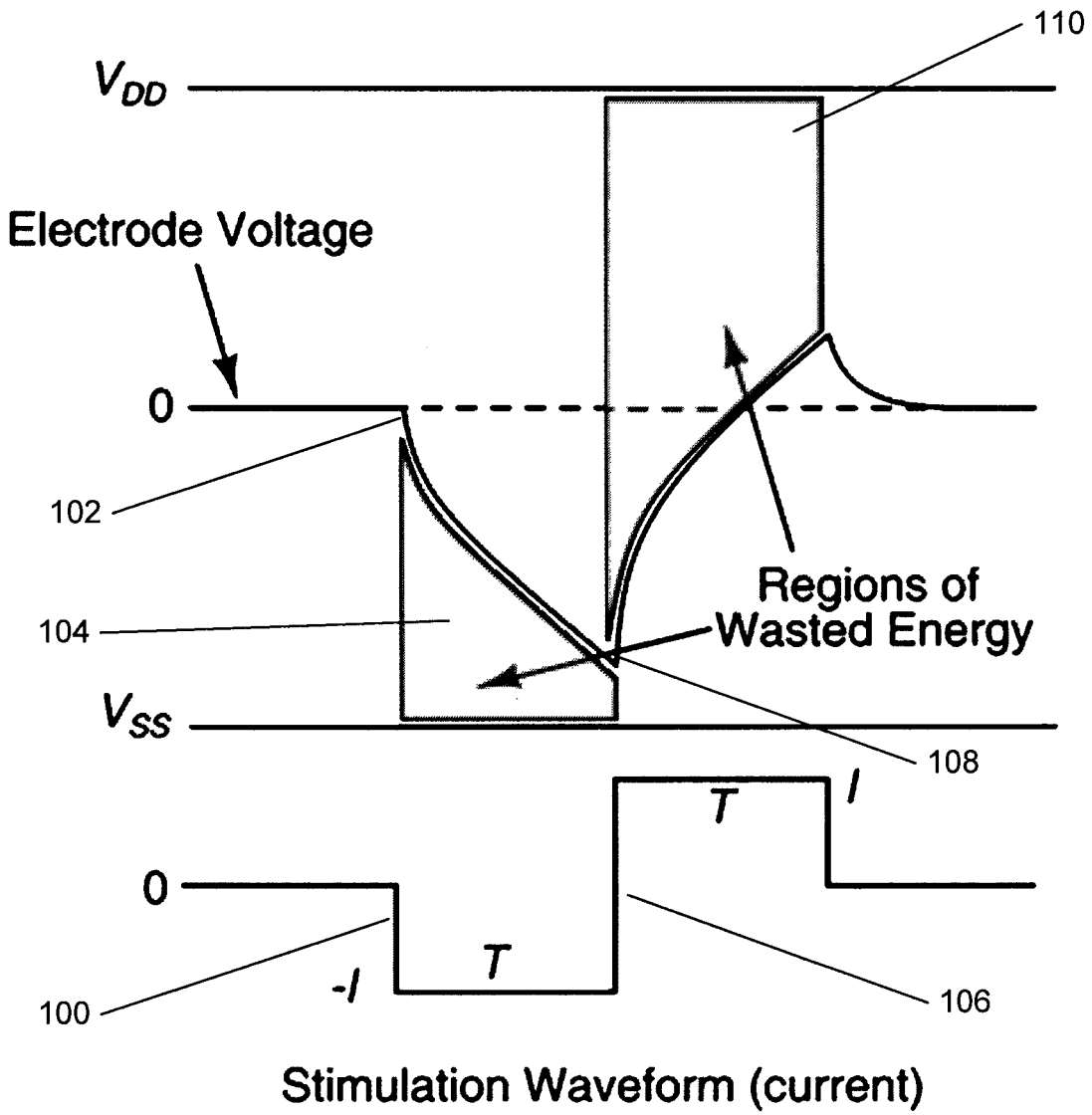
FIG. 3 is a graph illustrating amounts of wasted energy in the current sources of the electrode stimulator circuits shown in FIGS. 2a and 2b.

FIG. 3 is a graph illustrating amounts of wasted energy in the current sources of the electrode stimulator circuits shown in FIGS. 2a and 2b. In FIG. 2a, capacitor 22 ($C_{dl}$) is initially uncharged and electrode 20 is floating. Current source 34 ($I_{CS,N}$) is then turned on, connecting electrode 20 to power supply 32 ($V_{SS}$). Initially, as there is no charge on capacitor 22 ($C_{dl}$), most of the energy taken from power supply 32 is wasted in current source 34 ($I_{CS,N}$). As the stored energy in capacitor 22 ($C_{dl}$) increases and the voltage magnitude across capacitor 22 ($C_{dl}$) increases, the voltage drop and instantaneous energy dissipated in current source 34 ($I_{CS,N}$) decreases. In FIG. 3, at point 100, when electrode 20 is connected to current source 34, the voltage across the electrode begins to drop, resulting in wasted energy illustrated by area 104 of FIG. 3.

Similarly, during the discharge cycle, electrode 20 is connected to power supply 28 ($V_{DD}$) via current source 30 ($I_{CS,P}$). Once again, energy is dissipated in current source 30. In FIG. 3, at point 106, electrode 20 is connected to power supply 28. As such, the voltage across the electrode begins to raise at point 108, resulting in wasted energy illustrated by area 110 of FIG. 3. It should be noted that FIG. 3 does not depict the energy stored in capacitor 22, which is also partly dissipated in resistor 24.

As a general rule, for any given charge-transfer requirement within a given time interval, the use of a constant current spanning the whole interval minimizes the losses in the solution resistance ($R_S$). Current-source-based stimulators achieve this condition naturally, but themselves dissipate power thereby wasting a substantial amount of energy. The currents produced by adiabatic switched-capacitor-based stimulators tend to be exponential in nature because a step change in stimulator voltage leads to an exponential decay in current due to the first order RC circuit created by the electrode's impedance. An adiabatic voltage-based stimulator that also provides a constant, controlled current, therefore, results in the highest possible energy efficiency.

To control and, for example, in some desired applications, minimize the energy losses illustrated in FIG. 3, therefore, the present system provides an adaptive voltage-based stimulator that uses inductive energy storage to adiabatically drive one or more electrodes. The present system may be configured to drive the electrode using a continuum of possible voltages rather than a selected number of discrete steps, such as those offered by a capacitor bank. Additionally, in the present system, electrode current is sensed and regulated to a desired level using feedback adjustment of the adaptive voltage stimulator output voltage, even as the electrode voltage is changing (such as when the system operates in a stimulating down-conversion mode or a recycling up-conversion mode). In other words, as a current flowing through the electrode diverges from the charging current, a feedback loop integrated into the present system adapts and continuously servos the adaptive voltage stimulator output voltage to maintain the appropriate current level within the electrode without using dissipative current sources or limiters.

Additionally, in the present system, energy stored in the capacitance of the electrode is recoverable, and the present stimulator can be configured to recover at least a portion of that energy.

Figure 4:
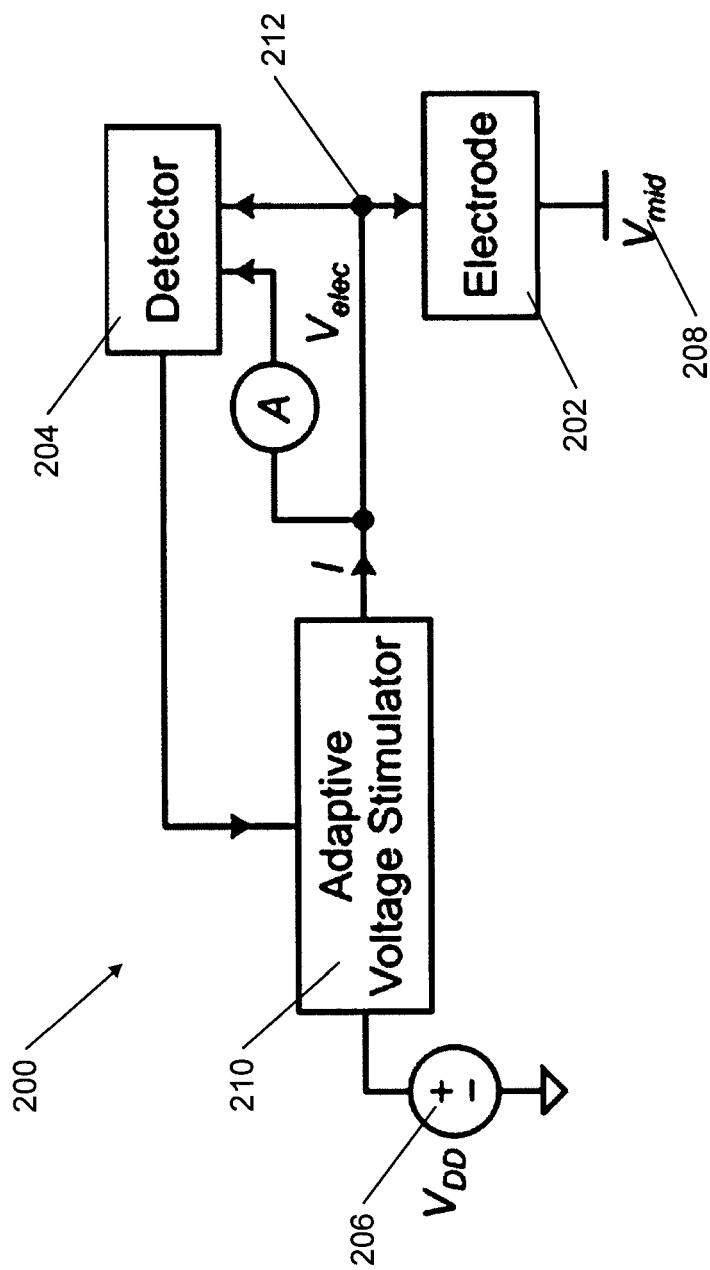
FIG. 4 is a block diagram illustrating functional components of a voltage-based stimulator system configured in accordance with the present disclosure.

FIG. 4 is a block diagram illustrating functional components of voltage-based stimulator system 200 configured in accordance with the present disclosure. Stimulator 200 includes adaptive voltage stimulator 210 that is connected to voltage source 206 and electrode 202 having an internal capacitance and resistance. Adaptive voltage stimulator 210 is configured to deliver energy to electrode 202 or, in a reverse operation, recover energy from electrode 202. Detector 204 detects a current passing through, or a voltage across, electrode 202 and feeds that information back to adaptive voltage stimulator 210. Based upon the fed-back information, adaptive voltage stimulator 210 controls energy delivery to or recovery from electrode 202 to ensure electrode 202 is operating in accordance with system requirements.

Adaptive voltage stimulator 210 can be implemented as a DC-DC converter that is controlled to maintain $V_{elec}$—the voltage across electrode 202—(see node 212 of FIG. 4) at a potential that is both approximately the same as the voltage across the capacitor ($C_{dl}$) of electrode 202 and that is consistent with a desired constant electrode stimulation current. Current sensing can be performed using a sensor coupled to detector 204. Detector 204, in one implementation, is configured to use a shunt topology or arrangement rather than a series topology to minimize losses within detector 204, although other current sensing systems could be used, as described below.

In stimulator 200 a single power supply 206 ($V_{DD}$) can be used with midrail voltage source or reference 208 ($V_{mid}$) at the return side of the electrode rather than a ground. As such, extreme conversion ratios and the need for a second converter to provide negative voltages can be avoided. Accordingly, in stimulator 200 the only sources of dissipation are the solution resistance intrinsic to the electrode, and the imperfect efficiency of the adaptive voltage stimulator.

FIG. 5a is a block diagram showing additional detail of the functional components of electrode stimulator 300 configured in accordance with the present disclosure. Stimulator 300 includes two feedback loops for controlling the adaptive voltage stimulator. Specifically, stimulator 300 includes an inner control loop 302 and an outer control loop 304. The general operation of the stimulator 300 and, specifically, inner control loop 302 and outer control loop 304 will be described followed by a detailed description of the components and operation of the inner control loop 302 and outer control loop 304. Together, inner control loop 302 and outer control loop 304 make up a control circuit that controls the operation of the electrode stimulator and, thereby, energy delivery to or recovery from an electrode.

In general, outer control loop 304 is a slower control loop that controls current flow through the electrode, while inner control loop 302 is a faster control loop that controls voltage across the electrode. For each execution of outer loop 304, inner loop 302 is executed multiple times. Outer loop 304 receives an input from a controller that may or may not be integrated into the present stimulator system that is indicative of an amount of energy (e.g., current flow) to be delivered to the electrode. Outer loop 304 monitors a power characteristic (e.g., current flow, voltage, or power) through the electrode, compares the measured power characteristic to a desired value, and, if the measured value does not match the desired value (i.e., in stimulating down-conversion mode the measured value is too low, or in recycling up-conversion mode the measured value is too high), adjusts a set voltage value either higher or lower and then passes the set voltage value to inner loop 302.

Inner loop 302 receives the set voltage value that describes a particular voltage (though in other implementations, the set voltage value could be replaced with a set current, or set power value) to be achieved across the electrode and compares the value to a measured voltage across the electrode. If the two values diverge (i.e., in stimulating down-conversion mode the measured voltage is too low, or in recycling up-conversion mode the measured voltage is too high), inner loop 302 transmits a signal to the stimulator core (e.g., a power source connected to the electrode) instructing the stimulator core to deliver energy to, or recover energy from, the electrode to move the measured voltage across the electrode towards the desired value.

In particular, with detailed reference to FIG. 5a, inner feedback loop 302 is configured to control an operation of adaptive voltage stimulator core 310 for delivering energy to electrode 306. Inner feedback look 302 includes adaptive voltage stimulator core 310 that is connected to electrode 306, which, in turn, is connected to $V_{mid}$ supply 312. Digital to analog converter (DAC) and comparator 314 is connected to electrode 306 and pulse generator 308. Pulse generator 308 is connected to adaptive voltage stimulator core 310 and is configured to supply electronic pulses or signals to core 310 to control its operation and energy delivery to electrode 306.

Inner feedback loop 302 continually measures a voltage or other power characteristic across electrode 306 ($V_{elec}$) and compares that voltage to a set voltage value received from outer loop 304 via set voltage line 316. This comparison is performed by DAC and comparator 314. After comparing the measured voltage with the set voltage, DAC and comparator 314 transmits an indication of the difference to pulse generator 308. Pulse generator 308, in turn, controls an operation of adaptive voltage stimulator core 310 to provide energy to, or remove energy from, the electrode based upon the information received from DAC and comparator 314 and the current set voltage value.

In one implementation, the set voltage value received from outer loop 304 is a binary number (e.g., an 8-bit value). In that case, the set voltage value can be used to operate a set of switches inside DAC and comparator 314, which redistribute the charge that was acquired when $V_{elec}$ was sampled, effectively subtracting the value of $V_{elec}$ from the set voltage value. When combined with a comparator, this procedure allows DAC and comparator 314 to generate an output indicative of whether $V_{elec}$ was greater than or less than the set voltage. In one implementation, in stimulating down-conversion mode, the output of DAC and comparator 314 is high when $V_{elec}$ is less than the set voltage and low when $V_{elec}$ is greater than the set voltage. The output of DAC and comparator 314 is reversed when in recycling up-conversion mode. The output generated by DAC and comparator 314 can then be used to control the operation of pulse generator 308 to deliver the appropriate current to electrode 306.

Unlike conventional DC-DC converters, adaptive voltage stimulator core 310 can operate both forwards and backwards, delivering energy to or recovering energy from electrode 306. In the stimulating down-conversion mode, if DAC and comparator 314 determine that $V_{elec}$ has a value below set voltage 316, pulse generator 308 causes adaptive voltage stimulator core 310 to operate for one or more cycles, causing energy to be supplied to electrode 306 and, consequently, $V_{elec}$ to rise. If $V_{elec}$ has a value above set voltage 316, however, pulse generator 308 takes no action as sufficient energy is already delivered to electrode 306. In that case, the output capacitor of core 310 (see capacitor 408 of FIG. 6a, for example) is storing enough energy from prior pulsations of pulse generator 308 that core 310 can continue to supply energy to electrode 308 allowing pulse generator 308 to rest for another cycle. In contrast, in a recycling up-conversion mode, these operations are reversed. If DAC and comparator 314 determine that $V_{elec}$ has a value above a set voltage 316, the operation of pulse generator 308 is reversed causing adaptive voltage stimulator core 310 to lower $V_{elec}$, thereby returning energy to core 310. Conversely, if $V_{elec}$ has a value below set voltage 316, pulse generator 308 takes no action as sufficient energy has already been recovered from electrode 306. In that case, the output capacitor of core 310 (see capacitor 408 of FIG. 6a, for example) is sufficiently depleted from prior cycling that electrode 306 will passively transfer energy stored within electrode 306 to core 310 allowing pulse generator 308 to rest for another cycle. Example implementations and operation of pulse generator 308 and adaptive voltage stimulator core 310 are described below and illustrated in FIG. 8 and FIG. 6a, respectively.

The mode of operation of pulse generator 308 (either in stimulating down-conversion or recycling up conversion mode) can be controlled by the STIM/REC value that is communicated to the output switch network 326 of pulse generator 308 by a controller (e.g., controller 10 of FIG. 1 or another controller in communication with the components of stimulator 300), where a high value of STIM/REC indicates the stimulator is in stimulating down-conversion mode, while a low value of STIM/REC indicates the stimulator is in recycling up-conversion mode. Depending upon the value of STIM/REC, the switches in network 326 are commutated resulting in an inverted operation of core 310.

Outer loop 304 comprises current sensor 320, comparator 324, and counter 322. Outer loop 304 is configured to receive an input $V_{cur}$ 318 from a controller (e.g., controller 10 of FIG. 1). The input $V_{cur}$ is used by outer loop 304 to determine a goal current flow through or energy delivery to electrode 306. Outer loop then compares the goal current flow with the actual current flow through electrode 306 and, based upon that comparison, outer loop 304 supplies a particular set voltage 316 to inner loop 302 for controlling a voltage across electrode 312.

In the implementation shown in FIG. 5a, outer loop 304 measures the current in electrode 306 via shunt sensing in current sensor 320 and operates in a symmetric manner for the stimulating down-conversion and recycling up-conversion modes of operation of stimulator 300. The output of current-sensor 320 is a voltage proportional to electrode 306 current which is compared to the voltage $V_{cur}$ by comparator 324. The desired set current 316 is then adjusted by counter 322 based upon the output of comparator 324.

If, in a stimulating-down conversion mode of operation (determined by the STIM/REC input to comparator 322), the measured current magnitude in outer loop 304 is too small, digital counter 322 increments the set voltage magnitude, for example, by a fixed number of least significant bits (LSBs). The number of LSBs can be denoted $D_{attack}$, where the greater the number of LSBs, the more aggressively the system will self-correct to a particular electrode current. If, however, the measured current magnitude is too large, counter 322 decrements the set voltage magnitude, for example, by a separate fixed number of LSB's denoted $D_{release}$. The state of counter 322, therefore, is used to establish set voltage 316 which, in turn, controls the operation of DAC and comparator 314 in inner loop 302.

In both modes of operation (i.e., stimulating down-conversion and recycling up-conversion), current flow through stimulator 300 is limited and set by the internal resistance of electrode 306 and the output voltage of adaptive voltage stimulator core 310. To assure stability, as described below, the slow outer loop can be configured to allow for the inner voltage loop to settle before it makes any adjustments to the set voltage. As described below, in particular implementations of the present system, the system operates in a number of phases, some overlapping and some distinct, that allow for harmonious operation of the inner and outer loops, where the timing of the operation of the inner and outer loops can be controlled by a clock, such as clock 328.

Stimulator 300 includes clock 328 that is in communication with the components of stimulator 300. Clock 328 provides a routine output signal that can be used by the various components of stimulator 300 to control their different phases of operation and to ensure that the different components are not interfering with one another. For example, as described below, clock 328 can be used to process DAC and comparator 314 through the different phases described below in reference to FIGS. 10, 11 and 12, including $\phi_{az}$, $\phi_{samp}$, $\phi_{amp,out}$, $\phi_{amp,in}$, $\phi_{redist}$, and $\phi_{latch}$. Similarly clock 328 is used to process current sensor 320 through its phases, including $\phi_1$, and $\phi_2$, and to ensure that the switches contained within stimulator core 310 are open during the sensing phases of current sensor 320, again, as described below. Clock 328 can also be used by a controller of stimulator 300 to control the operation of both inner and outer loops, for example, to provide sufficient time for inner loop 302 to settle before operation of outer loop 304.

During a single stimulation event, the stimulator system passes through two modes of operation as described above. During a first period of time, the stimulator operates in a stimulating down-conversion phase and during a second period of time, the stimulator operates in a recycling up-conversion phase. In one example operation of stimulator 300, to complete a stimulation event, a controller first puts the system in the stimulating down-conversion mode (e.g., by setting the STIM/REC variable to 'STIM') and applies a voltage 318 ($V_{cur}$) to the slow current control loop 304. Note, as described above, the controller may comprise a single controller device such as controller 10 illustrated in FIG. 1, or may comprise several separate controller devices, with some being external to stimulator 300, while others are integrated into stimulator 300.

Current sensor 320 then measures current flowing through electrode 306 by detecting an associated voltage across a capacitance of electrode 306 over a predetermined time period and compares the detected voltage against $V_{cur}$ using comparator 324. Comparator 324 outputs the difference between the detected voltage at the electrode and $V_{cu_r}$ as either a high or low value depending upon which voltage was greater to counter 322.

Counter 322 receives the high or low value reflecting whether the measured voltage ($V_{amp}$) was greater than $V_{cur}$ from comparator 324 and, increments or decrements the set voltage counter accordingly. In one implementation, in stimulating down-conversion mode, if $V_{amp}$ was less than $V_{cur}$ (e.g., counter 322 received a low value from comparator 324), counter 322 increments the counter by a number of bits defined as $D_{attack}$, otherwise counter 322 decrements the counter by a number of bits defined as $D_{release}$. Conversely, in recycling up-conversion mode, if $V_{amp}$ was greater than $V_{cur}$ (e.g., counter 322 received a high value from comparator 324), counter 322 decrements the counter by a number of bits defined as $D_{attack}$, otherwise counter 322 increments the counter by a number of bits defined as $D_{release}$. Table 1 illustrates the different behavior of counter 322 based upon input from current sensor 320. In other implementations, though, the output from comparator 324 and the associated behavior of counter 322 can be selected based upon preferred system implementation, for example by causing the output of comparator 324 to be inverted based on operational mode, in which case the behavior of counter 322 does not change based upon operational mode.

TABLE 1

| Input From Current Sensor Indicates: | Current Operating Mode | Counter Action |
|---|---|---|
| $V_{amp} < V_{cur}$ | stimulating down-conversion | increment counter (increase set voltage) |
| $V_{amp} > V_{cur}$ | stimulating down-conversion | decrement counter |
| $V_{amp} > V_{cur}$ | recycling up-conversion | decrement counter (decrease set voltage) |
| $V_{amp} < V_{cur}$ | recycling up-conversion | increment counter (increase set voltage) |

Because the counter contains a digital representation of set voltage 316, by incrementing or decrementing the counter based upon whether the measured voltage was less than or greater than $V_{cur}$, counter 322 can increase or decrease the value of set voltage 316 supplied to inner control loop 302. Because the operation of counter 322 is dependent upon whether the system is operating in stimulating down-conversion mode, or recycling up-conversion mode (i.e., by inverting the operation of counter 322 based upon the mode), the behavior of comparator 324 does not need to be adjusted based upon the current mode of operation. Of course, in other implementations, the behavior of comparator 324 could be inverted based upon mode, while the behavior of counter 322 does not change.

Moving to inner loop 302, DAC and comparator 314 receives set voltage 316 from counter 322 and also measures a voltage ($V_{elec}$) across electrode 312. DAC and comparator 314 then compare the set voltage with the measured voltage. While in stimulating down-conversion mode, if $V_{elec}$ is less than the set voltage, the output of DAC and comparator 314 goes high, otherwise the output is low. Conversely, in recycling up-conversion mode, if $V_{elec}$ is greater than the set voltage, the output of DAC and comparator 314 goes high, otherwise the output is low. The output of DAC and comparator 314 is fed into pulse generator 308.

Pulse generator 308 receives as input both the output of DAC and comparator 314 as well as set voltage 316. When the output of DAC and comparator 314 goes high, pulse generator 308 uses set voltage 316 to generate or identify a timing sequence for triggering switches $D_1$ and $D_2$ for controlling adaptive voltage stimulator core 310. Based upon the mode of operation of the stimulator (either in stimulating down-conversion mode or recycling up-conversion), the signals $D_1$ and $D_2$ can be transmitted to different configurations of switches within core 310 causing core 310 to either deliver energy to electrode 306 (i.e., in stimulating down-conversion mode) or recover energy from electrode 306 (i.e., in recycling up-conversion mode). Pulse generator can use a look-up table, or other database to determine the timing of signals $D_1$ and $D_2$ based upon the set voltage value, or can calculate the values in real-time. Alternatively, as described below, pulse generator 308 can use a combination of a lookup table or database with a delay line to generate the timing signals.

The timing sequence for signals $D_1$ and $D_2$ is selected to cause a particular amount of energy to be delivered to, or recovered from, electrode 306. Then, depending upon the mode of operation of stimulator 300 and the configuration of switch network 326 of FIG. 5a, the outputs of $D_1$ and $D_2$ from pulse generator 308 into switches $M_p$ and $M_n$ of core 310 can be configured to cause energy to be delivered to electrode 306 in stimulating down-conversion mode, or energy to be recovered from electrode 306 in recycling up-conversion mode.

Both inner loop 302 and outer control loop 304 repeat the above-described operations a number of times during stimulating down-conversion mode, with inner loop 302 repeating at a higher frequency than outer loop 304, as described below. After completion of the stimulating down-conversion mode period, the controller (e.g., controller 10 of FIG. 1 or another controller in communication with stimulator 300) puts the stimulator system in recycling up-conversion mode (e.g., by setting STIM/REC to a low value). Each of the inner loop 302 and outer loop 304 repeat the processes described above, but in recycling up-conversion mode.

FIG. 5b is a flow chart illustrating method 350 that may be implemented by a stimulator to deliver energy to, or recover energy from, an electrode. Method 350 can be implemented by stimulator 300 illustrated in FIG. 5b.

In step 352, the stimulator receives an input that identifies a desired current flow in an electrode. The input may be received from a controller that is external to the stimulator, or one that is integrated within the stimulator. The desired current flow is generally selected to implement some therapeutic stimulation to the region of a patient in which the electrode is situated.

In step 354, the stimulator measures an actual current flow through the electrode. The stimulator may use a shunt current sensor (such as the sensor illustrated in FIG. 13), or another suitable current sensor to measure the current flow through the electrode. The ordering of steps 352 and 354 can be reversed, or each step may be performed at approximately the same time.

In step 356, the stimulator determines whether it is operating in stimulating down-conversion mode (STIM/DOWN-CONVERSION), or recycling up-conversion mode (RECY/UP-CONVERSION). The stimulator's mode of operation will affect the set voltage value that the stimulator generates. When operating in stimulating down-conversion mode, in step 358, if the measured current was less than the desired current, the stimulator increases the set voltage value, otherwise the set voltage is decreased. When the stimulator is operating in recycling up-conversion mode, in step 360, if the measured current was less than the desired current, the stimulator decreases the set voltage value, otherwise the set voltage is increased.

Although steps 356, 358, and 360 are shown as separate steps in FIG. 5b, in some implementations, rather than explicitly determine the mode of operation of the stimulator, the outputs of the various components (such as comparators of amplifiers) of the stimulator are inverted, or automatically modified based upon the stimulator's current mode of operation. As such, the components of the stimulator may automatically modify their behavior (e.g., their output) based upon the stimulator's current mode to perform either of steps 358 and 360, making step 356 unnecessary.

Having established the set voltage value (either by step 358 or step 360), a voltage across the electrode is sampled in step 362. Then the stimulator again determines its current operating mode in step 364. As described above, though, this step may not be explicitly performed by the stimulator. Instead, the components of stimulator responsible for performing steps 366 or 368 may automatically modify their own output based upon the current mode of the stimulator, making step 364 unnecessary.

If the stimulator is in stimulating down-conversion mode, and the measured voltage across the electrode was less than the set voltage, in step 366 the stimulator identifies a sequence of electrical signals that, when communicated to control switches within the core or power supply of the stimulator, cause energy to be transmitted from the core to the electrode. The signals may comprise a sequence of digital pulses, analog waves, or other electrical stimuli configured to control a behavior of the core.

If the stimulator is in recycling up-conversion mode, and the measured voltage across the electrode was greater than the set voltage, in step 368 the stimulator identifies a sequence of electrical signals that, when communicated to the core or power supply of the stimulator, cause energy to be transmitted from the electrode to the core. The signals may comprise a sequence of digital pulses, analog waves, or other electrical stimuli configured to control a behavior of the core.

After establishing the appropriate signals in either step 366 or 368, the signals are communicated to the core of the stimulator in step 370. After completion of step 370, the stimulator may repeat the inner loop voltage measurement and comparison steps (e.g., inner loop 302 of FIG. 5a), or the outer loop current measurement and comparison steps (e.g., outer loop 304 of FIG. 5a). As described above, because the voltage comparison loop operates at a higher frequency than the current comparison loop, the stimulator will most often move from step 370 to step 362 to repeat the voltage comparison loop. However, depending upon the ratio of the number of times the voltage comparison loop is completed to the number of time the current comparison loop is completed, the comparator will occasionally move from step 370 to step 352, to repeat the current comparison loop.

In many electrode stimulating operations, the electrical stimuli delivered to an electrode are short in duration—sometimes being only a few hundreds of microseconds in duration. As such, the electrode voltage, starting at rest, will develop anywhere from several hundred millivolts to several volts and back to rest in a brief span of time. In conventional power converter applications, although load currents may vary over time, load voltages are typically fixed or vary only slowly. As such, conventional power converters do not usually need a very fast response time or a very wide output voltage range.

In electrode stimulation applications, though, relatively fast settling time to adapt to the quickly changing electrode voltage is important. This is true during transitions from positive to negative electrode current and vice versa where near-instantaneous changes in the IR voltage drop across an electrode's solution resistance are required. A converter that cannot change its output voltage quickly cannot quickly effect changes in electrode current.

Additionally, biphasic pulses, as required in electrode stimulation for the creation of charge-balanced waveforms for safe operation, require that a power converter be able to both source and sink current. This can be an unusual requirement as power converters typically deliver current to a load rather than draw current from a load. However, a single converter able to run in two directions allows for operation of the stimulator from a single power supply or stimulator core, and performance of energy recovery during a second, charge balancing phase of stimulation.

Figure 6A:
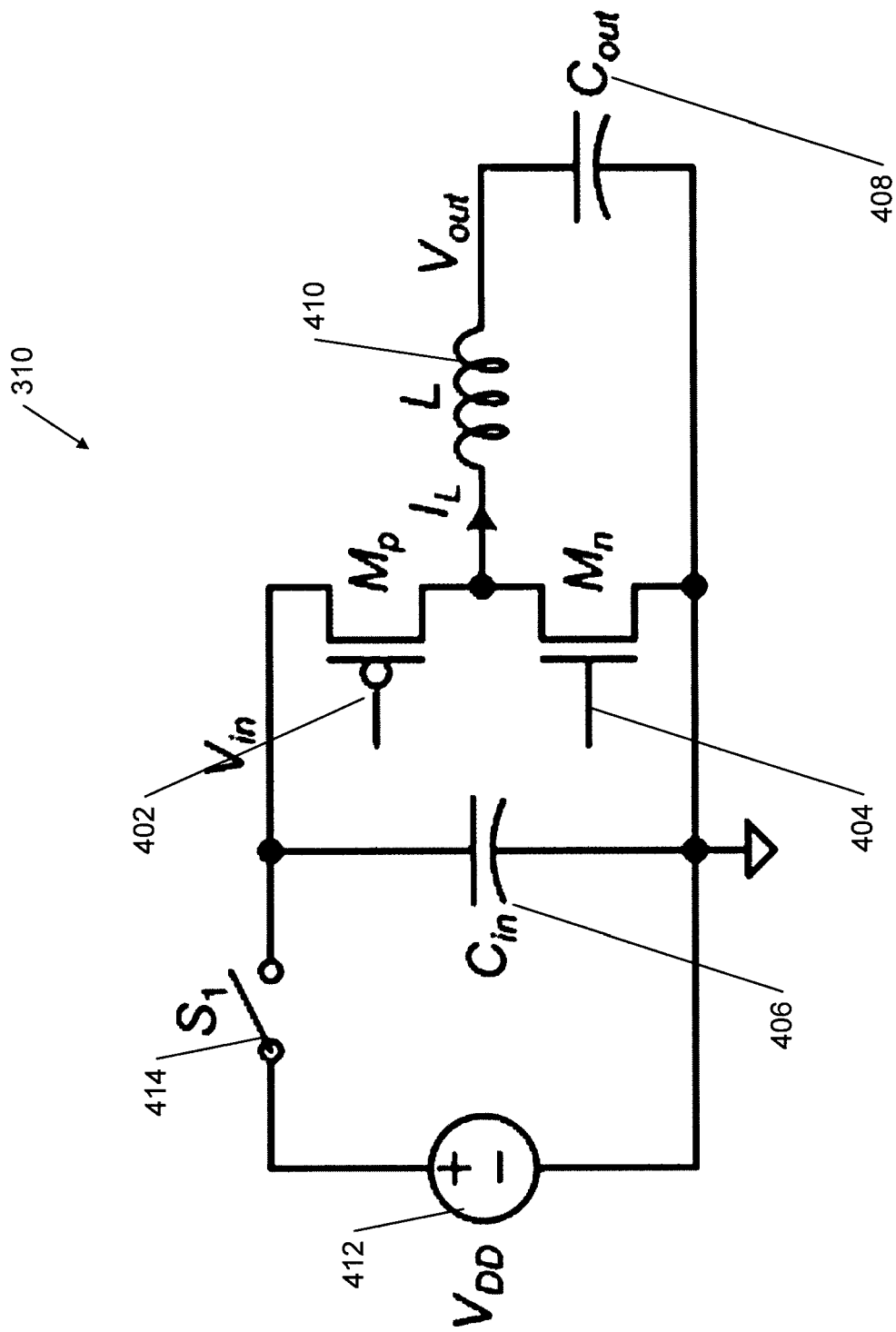
FIG. 6a is a schematic diagram representing an example implementation of adaptive voltage stimulator core for delivering energy to and recovering energy from an electrode for stimulation applications.

FIG. 6a is an illustration of an example implementation of adaptive voltage stimulator core 310 shown in FIG. 3 for delivering energy to and recovering energy from an electrode for stimulation applications. In the depicted configuration, stimulator core 310 is implemented as a buck converter. The output of core 310 (i.e., $V_{out}$) is controlled by manipulating switch 402 ($M_p$) and switch 404 ($M_n$) of stimulator core 310. Switches 402 and 404 may include transistors, diodes, or other switching devices that use an input signal to control the flow of electricity through the switching device. Depending upon the order with which switches 402 and 404 are manipulated, energy can be delivered from capacitor 406 to the output, or, alternatively, energy stored at the output can be transmitted back to capacitor 406. As shown in FIG. 5a, switches 402 and 404 are connected to, and can be manipulated by, pulse generator 308 to control an operation of stimulator core 310 and, ultimately, power delivery to or from the electrode.

When in a normal buck converter operation, $V_{out}$ is less than $V_{in}$ and energy is transferred from capacitor 406 to capacitor 408. This voltage down-conversion is achieved by first turning on switch 402 ($M_p$) to flux up inductor 410. Switch 402 ($M_p$) is then turned off and switch 404 ($M_n$) is then turned on causing energy stored in inductor 410 to be released to a load connected across $V_{out}$ (not shown), such as a connected electrode. In terms of the present disclosure, this conventional buck converter operation corresponds to the present stimulating down-conversion mode.

In the recycling up-conversion mode of operation (i.e., where $V_{out} V_{in}$), the switching order for switches 402 and 404 is commutated to reverse the flow of energy from the output (at a higher voltage) to the input (at a lower voltage). In the recycling up-conversion mode, switch 404 ($M_n$) is first turned on to negatively flux up inductor 410 by withdrawing energy from capacitor 408. Then, switch 404 ($M_n$) is turned off and switch 402 ($M_p$) is turned on, releasing the energy stored in inductor 410 into capacitor 406.

The switches 402 ($M_p$) and 404 ($M_n$) are controlled by signals (e.g., signals $D_1$ and $D_2$ in FIG. 5a) received from a pulse generator. To achieve the different modes of operation of adaptive voltage stimulator core 310, in one implementation, during stimulating down-conversion mode, signal $D_1$ controls switch 402 ($M_p$) while signal $D_2$ controls switch 404 ($M_n$) and during recycling up-conversion mode signal $D_2$ controls switch 402 ($M_p$) while signal $D_1$ controls switch 404 ($M_n$). Other switch configurations, though, can be utilized in accordance with the present disclosure. The allocation of a particular signal from the pulse generator to one of switches 402 and 404 can be controlled by a switch network such as network 326 of FIG. 5a.

Because this energy recycling is not 100% efficient in practice, and because there is dissipation in the load resistance (e.g., $R_s$), energy is periodically delivered from power source 412 ($V_{DD}$) to capacitor 406 by closing switch 414 to replenish charge loss in capacitor 406 over a cycle. In one implementation, capacitor 406 is replenished by closing switch 414 only at the beginning of each stimulation cycle (i.e., after completing the recycling up-conversion mode, but before entering the stimulating down-conversion mode).

Figure 6B:
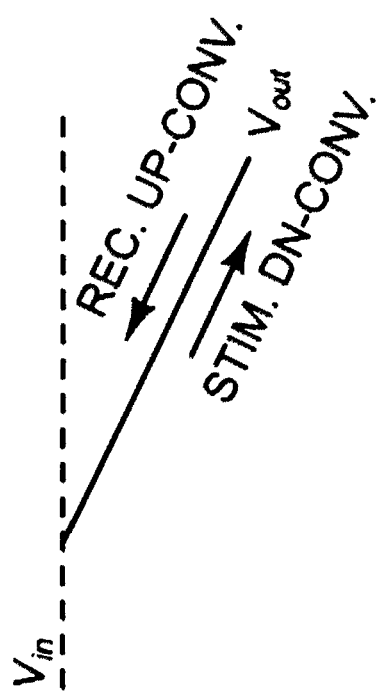

FIG. 6b is an illustration showing an idealized range of output voltages and flow of power for the adaptive voltage stimulator core shown in FIG. 6a. In the stimulating down-conversion mode (STIM. DN-CONV.) mode, energy is transferred from the source ($V_{in}$) to the electrode ($V_{out}$). In recycling up-conversion mode (REC. UP-CONV.), the reverse is true with energy being delivered from the electrode to the source.

Returning to FIG. 6a, in one implementation of the present system, a switching frequency of approximately 250 kHz for switches 402 and 404 provides an adequate compromise between speed and power consumption, as higher switching frequencies consume greater power in their control circuitry. In such a configuration, a neural stimulation pulse at 1 ms/phase would allow for 250 individual switching cycles per stimulation phase allowing for a reasonably accurate pulse shape. Furthermore, inductor 410 and capacitor 408 of FIG. 6a can be adjusted to meet the power and speed requirements of any individual application. In other applications, though, different switching frequencies with modified inductor 410 and capacitor 408 configurations can be used.

Because the present adaptive voltage stimulator can be configured to power a variety of loads, ranging from very light to moderate, the stimulator is configured to use a discontinuous conduction mode (DCM) and a pulse frequency modulated (PFM) control strategy.

Referring back to FIG. 5a, therefore, under PFM, the inner, voltage control loop 302 pulses supplied by pulse generator 308 (e.g., signals $D_1$ and $D_2$) are only transmitted as necessary and as determined by feedback monitoring of $V_{out}$ by DAC and comparator 314. As such, there is a maximum possible load current $I_{max\_load}$ that adaptive voltage stimulator core 310 can support, corresponding to a pulsing cycle occurring at every switching interval T. At lighter loads, the stimulator will pulse in any given switching interval with probability of activity $P_a$, resulting in an average apparent switching interval of $T_{apparent} = T/P_a$. The absolute duration of the switch signals $D_1$ and $D_2$ supplied by pulse generator 308, therefore, do not change with load. However, the frequency at which signals $D_1$ and $D_2$ pulse will change with load.

In one example, $D_1$ and $D_2$ represent the fractions of the nominal switching period T for which each signal enables the corresponding switches 402 ($M_p$) or 404 ($M_n$) (see FIG. 6a) respectively. Thus, when the stimulator pulses in the stimulating down-conversion mode, the energy taken from capacitor 406 of adaptive voltage stimulator core 310 is:

$$E_{C_{in}} = \frac{V_{in}(V_{in} - V_{out})}{2L} D_1^2 T^2. \tag{1}$$

However, because the stimulator may not be required to pulse at the maximum possible frequency, this energy will be consumed by the load over the interval $T_{apparent}$. The energy consumed by the load is:

$$E_{load} = V_{out} \times I_{load} \times T/P_a \tag{2}.$$

Equating $E_{C_{in}}$ and $E_{load}$, the following relationship for the adaptive voltage stimulator operating in DCM is established:

$$D_1^2 = \frac{2L \times V_{out} \times I_{load}/P_a}{V_{in}(V_{in} - V_{out})T}; \tag{3}$$

where $I_{load}$ is the average current into the electrode, $V_{in}$ and $V_{out}$ are the input and output voltages respectively, T is the available switching interval, L is the inductance of inductor 410, and $P_a$ is the probability that the adaptive voltage stimulator actually pulses during any given switching interval. The parameters $V_{in}$, L, $I_{load}$, and T are user-settable constants. It can be presumed that the change in $V_{out}$ in a given switching cycle is small such that $V_{out}$ can be considered constant throughout the cycle.

In designing $D_1$ and $D_2$, the adaptive voltage stimulator in stimulating down-conversion mode can be considered. In that case, the signal $D_1$ closes switch 402 ($M_p$), placing a voltage $V_{in} - V_{out}$ across the inductor, leading to a steady buildup of current in the inductor. Then, switch 402 ($M_p$) is opened and switch 404 ($M_n$) is closed according to $D_2$, placing a value of $-V_{out}$ across inductor 410.

To prevent an unlimited buildup of flux in inductor 410, the average voltage across the inductor should be approximately zero across the two phases (stimulating down-conversion and recycling up-conversion). This condition leads to the relationship between $D_1$ and $D_2$ shown in Equation 4.

$$D_2 = \frac{V_{in} - V_{out}}{V_{out}} \times D_1. \quad (4)$$

One strategy for satisfying Equation 4 is to select $D_1$ to be constant and $D_2$ variable according to $V_{out}$. In that case, though, the effect of the $D_1$ signal would depend upon the magnitude of $V_{out}$. A single pulse of $D_1$ would cause a large increase in $V_{out}$ if $V_{out}$ were very low, but only a small increase in $V_{out}$ if $V_{out}$ were already large. Although this may be acceptable if there is a large filtering capacitor at the output, it may not be acceptable for a stimulator implementation where there isn't a large filtering capacitor and the aim of the system is to adjust the output voltage quickly and uniformly over a wide range. Accordingly, it would be preferable (though not required) to determine a scheme for $D_1$ and $D_2$ that causes the same change in $V_{out}$ per pulse, independent of the present value of $V_{out}$.

If Equation 3 is substituted for $D_1$ in Equation 4, the product of $D_1$ and $D_2$ is a constant independent of $V_{out}$.

$$D_1 \times D_2 = \frac{2LI_{load}/P_a}{V_{in}T}. \quad (5)$$

Thus, as the desired $V_{out}$ changes, the ratio of $D_1$ and $D_2$ is adjusted in a feed-forward manner to satisfy Equation 4 while simultaneously keeping the product of $D_1$ and $D_2$ constant to satisfy Equation 5. If both conditions are satisfied, whenever the converter pulses, the charge packet delivered per pulse and change in $V_{out}$ immediately following the pulse are invariant with $V_{out}$. This property provides predictable operation of the adaptive voltage stimulator, regardless of the value of $V_{out}$. It should be noted that these calculations are based upon the stimulator operating in stimulating down-conversion operation, but apply equally to recycling up-conversion mode, as the topology and circuitry are the same only with the direction of current flow reversed.

Figure 8:
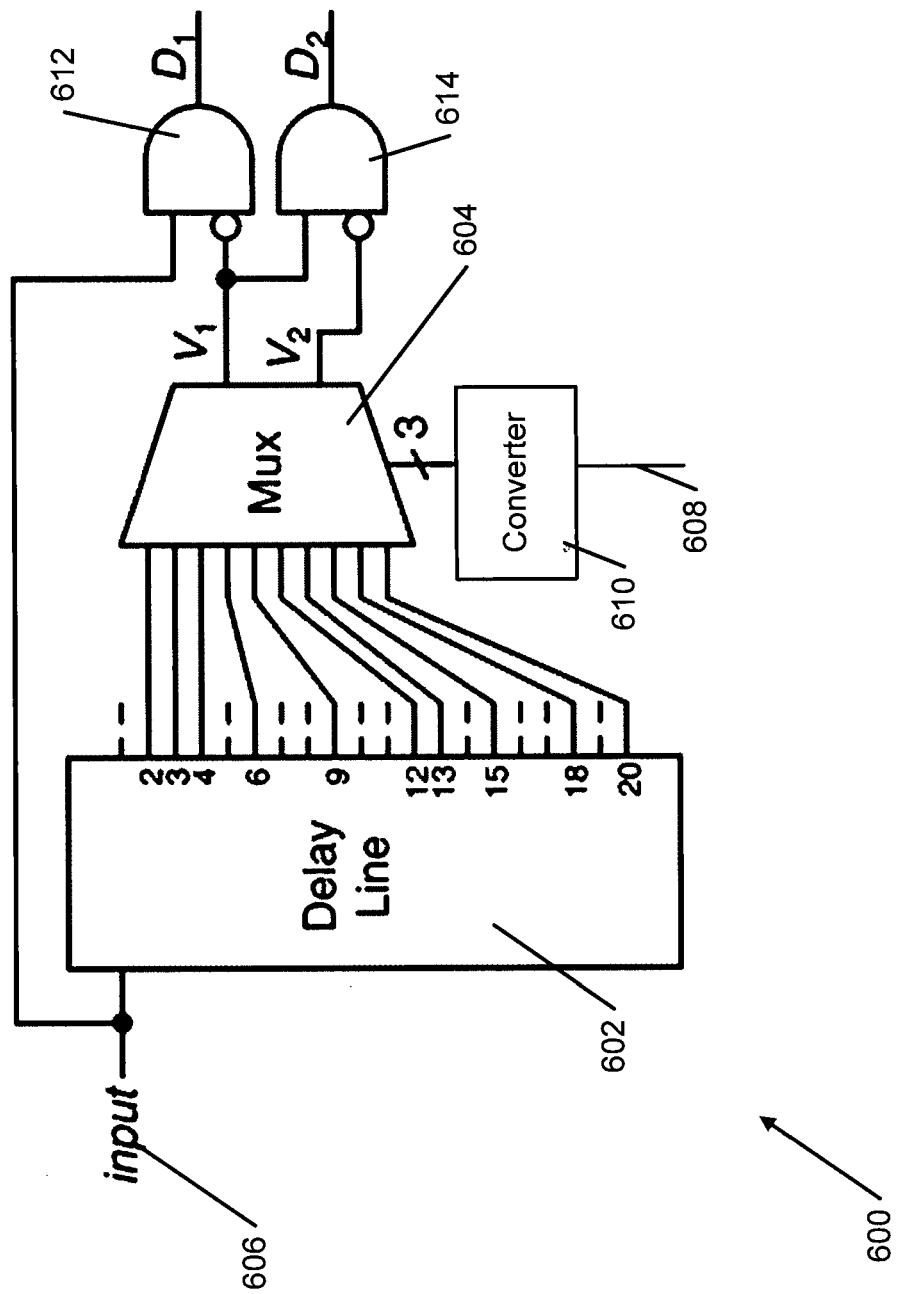
FIG. 8 is a schematic diagram showing an example pulse generator circuit for transmitting switching signals to an adaptive voltage stimulator core.

FIG. 8 is a schematic diagram showing an example pulse generator circuit for transmitting the switching signals $D_1$ and $D_2$ to the adaptive voltage stimulator core of FIG. 5a and may be used, for example, to implement pulse generator 308 of FIG. 5a. In general, the pulse generator may include any circuit or device configured to transmit pulses to stimulator core 310 based upon a comparison of a measured voltage across an electrode to a desired set voltage for delivering energy to, or removing energy from the load. For example, pulse generators that comprise microprocessors or other circuitry programmed to transmit the desired switching signals can be used in conjunction with the present electrode stimulation system.

Pulse generator 600 includes delay line 602. Input 606 to delay line 602 receives the output from DAC and comparator 314 (see FIG. 5a). In stimulating down-conversion mode, input 606 stays low until $V_{elec}$ is less than the set voltage, at which point input 606 goes high. Conversely, in recycling up-conversion mode, input 606 stays low until $V_{elec}$ is greater than the set voltage. After input 606 is sampled by pulse generator 600, input 606 goes low until the next time DAC and comparator 314 (see FIG. 5a) compare $V_{elec}$ with the set voltage, at which time input 606 may remain low, or go high.

After input 606 goes high, the various pins (e.g., pins 1-20) of delay line 602 switch from low to high outputs according to the programmed operation of delay line 602. In the present implementation, at one tap (e.g., clock cycle, or predetermined number of clock cycles) after input 606 goes high, pin 1 of delay line 602 goes high. At two taps after input 606 goes high, pin 2 of delay line 602 goes high. At three taps after input 606 goes high, pin 3 of delay line 602 goes high, and so on.

Pulse generator 600 also receives as an input set voltage 316 (see FIG. 5a) which is fed into input 608 and includes a representation of the current set voltage established by the slow outer control loop 304 (see FIG. 5a). The representation can be binary having any number of appropriate bits, or analog, depending upon system implementation.

In pulse generator 600, the set voltage value is fed into converter 610 which converts the set voltage value into an identification of two taps (or pins) of delay line 602 that are used for controlling the transmission of signals $D_1$ and $D_2$ by pulse generator 600. To identify the two taps, converter 610 can use a lookup table or other database for deriving the $D_1$ and $D_2$ signal timings, or may calculate the values in real time. Table 2 gives example mappings from input set voltage to $D_1$ and $D_2$ signal timings.

TABLE 2

| $S_2$ | $S_1$ | $S_0$ | $V_1$ tap ($D_1$ Length) | $V_2$ tap | $D_2$ Length | Ratio | Vout/Vin | Voltage Range (3.3 V scale) in Stimulating Down-conversion Mode | Voltage Range (3.3 V scale) in Recycling Up-conversion Mode |
|---|---|---|---|---|---|---|---|---|---|
| 0 | 0 | 0 | 2 | 20 | 18 | 2:18 | 0.1 | 0-0.32 V | 0.65-0.32- V |
| 0 | 0 | 1 | 3 | 15 | 12 | 3:12 | 0.2 | 0.33-0.65 V | 1.01-0.66 V |
| 0 | 1 | 0 | 4 | 13 | 9 | 4:9 | 0.31 | 0.66-1.01 V | 1.64-1.02 V |
| 0 | 1 | 1 | 6 | 12 | 6 | 6:6 | 0.5 | 1.02-1.64 V | 2.27-1.65 V |
| 1 | 0 | 0 | 6 | 12 | 6 | 6:6 | 0.5 | 1.02-1.64 V | 2.27-1.65 V |
| 1 | 0 | 1 | 9 | 13 | 4 | 9:4 | 0.69 | 1.65-2.27 V | 2.63-2.28 V |
| 1 | 1 | 0 | 12 | 15 | 3 | 12:3 | 0.8 | 2.28-2.63 V | 2.96-2.64 V |
| 1 | 1 | 1 | 18 | 20 | 2 | 18:2 | 0.9 | 2.64-2.97+ V | 3.3-2.97 V |

As shown in Table 2, given a particular set voltage range (either in stimulating down-conversion or recycling up-conversion mode), converter 610 selects a corresponding three-bit output $S_0$, $S_1$, and $S_2$ that defines a combination of taps that control the transmission of signals $D_1$ and $D_2$. The three-bit output $S_0$, $S_1$, and $S_2$ is then fed into multiplexer (mux) 604 which uses the three bit output from converter 610 to inspect particular pins on delay line 602 for controlling transmission of signals $D_1$ and $D_2$. The tap positions of Table 2 are setup so that the product of the number of delay units for $D_1$ and $D_2$ is constant across all settings (i.e., 36 in Table 2).

For example, if pulse generator 600 is operating in stimulating down-conversion mode, the set voltage value equates to 0.1V, and input 606 goes high, converter 610 will select the first row of Table 2 to identify the $D_1$ and $D_2$ signal sequence and transmits $S_0$, $S_1$, and $S_2$ values of 0, 0, and 0 to mux 604. In row 1, $D_1$ is assigned tap number 2, while $D_2$ is assigned tap number 20.

The first row configuration causes mux 604 to transmit a high $V_1$ output when pin 2 of delay line 602 goes high, and a high $V_2$ output when pin 20 of delay line 602 goes high. That output from mux 604 causes pulse generator 600 to begin transmitting the $D_1$ signal when input 606 goes high, and stop transmitting the $D_1$ signal when the high input value appears on pin 2 of delay line 602 (causing $V_1$ to go high). When pin 2 goes high and pulse generator 600 stops transmitting signal $D_1$, pulse generator 600 begins transmitting signal $D_2$. Pulse generator 600 continues to transmit signal $D_2$ until the high input value appears on pin 20 (causing $V_2$ to go high).

As such, in this example, at a set voltage value between 0-0.32 V, the ratio of time that $D_1$ is transmitted versus $D_2$ is 2:18. Because, at such a low voltage, the output inductor (e.g., inductor 410 of FIG. 6a) will flux up quickly, the short duration of the $D_1$ signal with respect to the $D_2$ signal is appropriate. Also, because inductor 410 (see FIG. 6a) requires sufficient time to deliver that energy to the load, the extended duration of the signal $D_2$ is appropriate. Conversely, in stimulating down-conversion mode where the set voltage is relatively high, the relative durations of signals $D_1$ and $D_2$ are reversed—with a relatively high output voltage at the electrode, it will take more time to flux up the output inductor, but less time to discharge that energy to the load.

As can be seen from Table 2, in recycling up-conversion mode, the voltage ranges are offset by one row from the equivalent stimulating down-conversion voltage ranges, resulting in slightly different $D_1$ and $D_2$ signal timing for stimulating down-conversion mode compared to recycling up-conversion mode for a given set voltage. In other implementations, though, the voltage ranges for each row in table 1 are the same, regardless of the mode. In that case, pulse generator 600 selects the same $D_1$ and $D_2$ signal timings based on a voltage, regardless of the current mode of operation, and relies on switch network 326 to ensure that the $D_1$ and $D_2$ signals are delivered to the correct switches of core 310 to ensure that either energy is delivered to or removed from the electrode based upon the current mode of operation of the simulator.

Table 2 is just one example mapping from a set voltage value to a sequence for transmitting the $D_1$ and $D_2$ signals. Other mappings may include an increased number of taps allowing for the set voltage values (and corresponding output sequences of the $D_1$ and $D_2$ signals) to be more finely adjusted. Furthermore, the ranges of voltages assigned to a particular $D_1$ and $D_2$ signal sequence can be adjusted or modified. In Table 2, above, the voltage ranges are selected based upon the ratio of $D_1$ signal duration to $D_2$ signal duration, with each ratio defining the edges of a group of voltages. In other implementations, the ratio of $D_1$ to $D_2$ signal duration could be used to define a center point in the voltage range associated with each $D_1$-$D_2$ sequence.

Accordingly, in one implementation, delay line 602 includes 20 unit elements as shown in FIG. 8. Multiplexer 604 receives input from delay line 602 and selects two outputs from the delay line based on the current set value of $V_{out}$ (i.e., set voltage 316 of FIG. 5a). The two outputs, denoted $V_1$ and $V_2$, are then used to generate the signals $D_1$ and $D_2$ which are, in turn used to control the operation of adaptive voltage stimulator core (e.g., core 310 of FIG. 5a).

Figure 9:
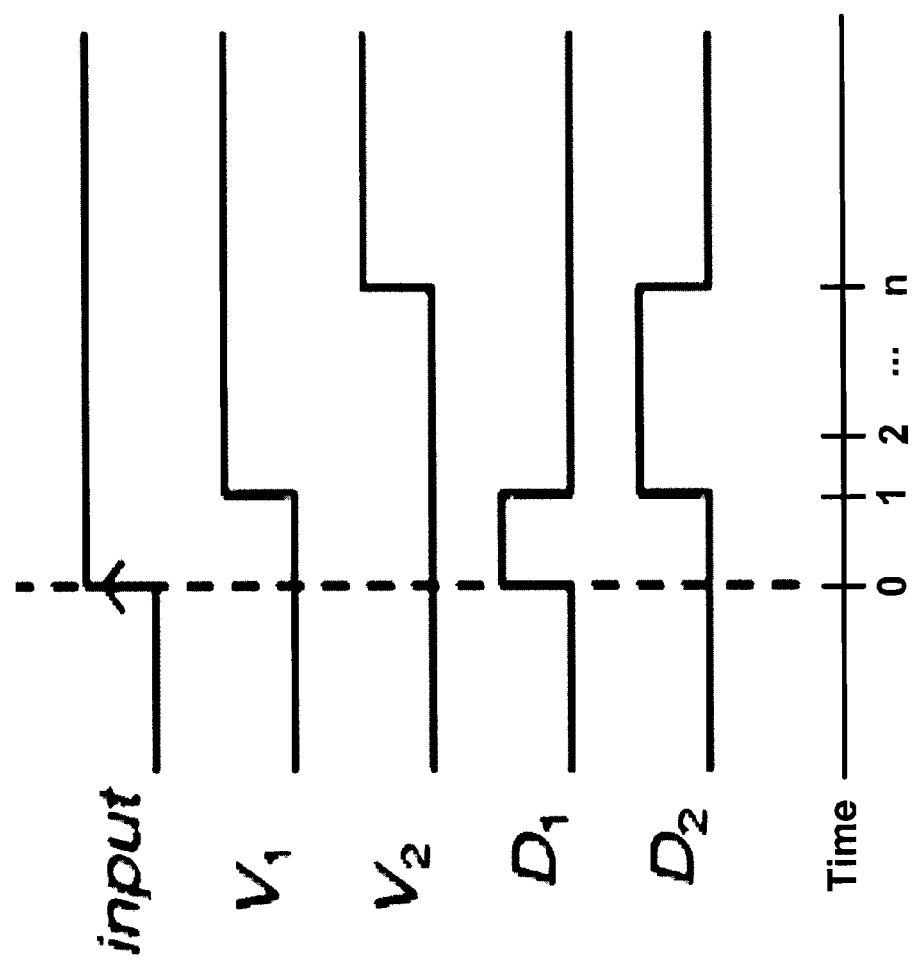
FIG. 9 is a timing diagram showing example output of the pulse generator circuit of FIG. 8 given a particular sequence of inputs.

FIG. 9 shows example output of the pulse generator circuit of FIG. 8 given a particular input. In this example, the set voltage value at input 608 causes converter 610 to select tap number 1 to control the transmission of signal $D_1$ and tap number 'n' to control the transmission of signal $D_2$. As such, when input 608 goes high, pulse generator 600 begins transmitting $D_1$, does not transmit $D_2$, and monitors the output of pin 1 ($V_1$) on delay line 602. At tap number 1, $V_1$ goes high (i.e., the output at pin 1 of delay line 602 goes high) and pulse generator 600 stops transmitting $D_1$. When $V_1$ goes high, pulse generator 600 begins transmitting signal $D_2$ and monitors the output of pin n ($V_2$) on delay line 602. At tap number n, $V_2$ goes high (i.e., the output at pin n of delay line 602 goes high) and pulse generator 600 stops transmitting signal $D_2$. This behavior is determined by logic gates 612 and 614 of pulse generator 600 as shown in FIG. 8.

Referring to FIG. 8, logic gate 612 controls the transmission of signal $D_1$. Gate 612 is an AND gate with inputs of input 606 and not $V_1$, where $V_1$ represents the output of the tap selected for signal $D_1$ from delay line 602. Gate 614 is an AND gate with inputs of $V_1$ and not $V_2$, where $V_2$ represents the output of the tap selected for signal $D_2$ from delay line 602. Upon input 606 going high, the inputs to gate 612 are both high (input 606 is high, and $V_1$ remains low, but is inverted) and signal $D_1$ is transmitted. At that time, because $V_1$ is not high, both inputs to gate 614 are not high and signal $D_2$ is not transmitted.

When $V_1$ goes high (i.e., the pin of delay line 602 representing the tap selected for $D_1$ goes high) both inputs to gate 612 are not high (the not $V_1$ input is now low), and $D_1$ is not longer transmitted. At the same time, though, both inputs to gate 614 are high ($V_1$ has just turned high and $V_2$ has not yet gone high, but the $V_2$ input is inverted) so $D_2$ is transmitted. When $V_2$ goes high (i.e., the pin of delay line 602 representing the tap selected for $D_2$ goes high) both inputs to gate 614 are not high, and $D_2$ is not longer transmitted.

The implementations of pulse generator 600 shown in FIG. 8, the associated timing illustration shown in FIG. 9, and Table 1 described above are only example implementations of a pulse generator configuration to control power delivery to (or recovery from) the electrode of the present system. Other systems can be implemented that use, for example, a comparison of the particular voltage across the electrode to a set voltage value as well as the set voltage value itself to determine an appropriate switching algorithm for power delivery.

Figure 7:
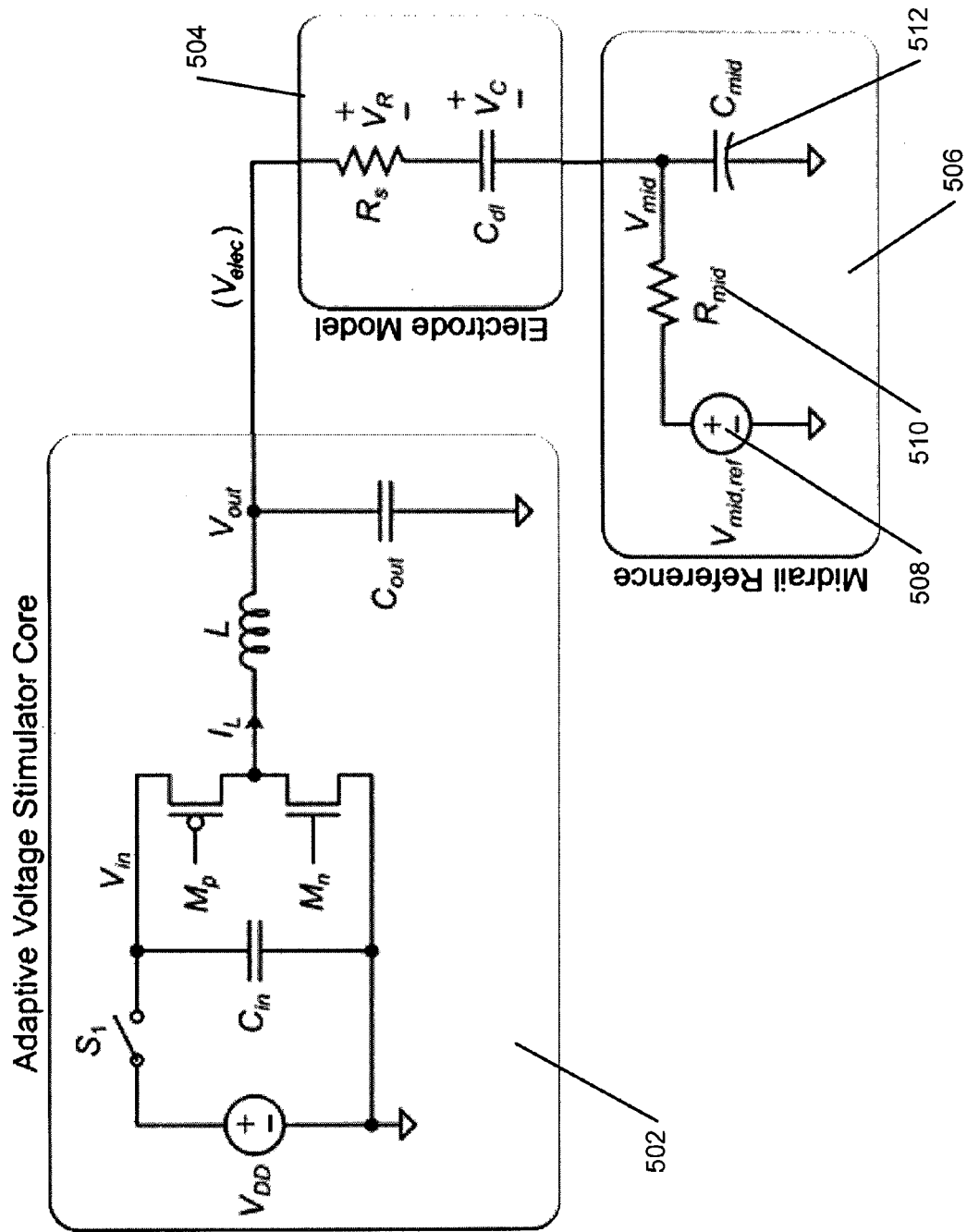
FIG. 7 is a schematic diagram showing components of an adaptive voltage stimulator including an adaptive voltage stimulator core, electrode model, and midrail reference.

FIG. 7 shows components of an adaptive voltage stimulator including adaptive voltage stimulator core 502, electrode model 504, and midrail reference 506. Midrail reference 506 can be used, for example, to implement $V_{mid}$ 312 of FIG. 5a. Although in some system implementations a second electrode completes the circuit, in the example shown in FIG. 7, the model of any such return electrode has been omitted by combining the return electrode model with that of the stimulating electrode into a single electrode model 504. As such, the remote end of electrode 504 corresponds to the bulk tissue whose potential has been set to $V_{mid}$ by the midrail voltage reference 506, halfway between the power supply voltage ($V_{DD}$) and ground. By maintaining the bulk tissue at the intermediate voltage supplied by midrail reference 506, a single adaptive voltage stimulator can drive the stimulating electrode both above and below $V_{mid}$.

Because stimuli are designed to be charge neutral on average, it is not necessary for the midrail reference to supply DC current. Accordingly, the role of midrail reference 506 in the circuit of FIG. 7 is, in some ways, limited to being a reference. For that reason, $V_{mid}$ can be generated using the voltage reference $V_{mid,ref}$ 508 and a large-valued RC filter network consisting of $R_{mid}$ 510 and $C_{mid}$ 512, as shown in FIG. 7. Without this filter, the instantaneous electrode current would both enter and leave midrail reference 506, requiring midrail reference 506 to be a genuine DC supply. With the filter in place, though, midrail reference 506 can be a high impedance voltage reference. Thus, $R_{mid}$ 510 can be explicit or implied in the output impedance of $V_{mid,ref}$ 508.

During stimulation, therefore, $C_{mid}$ 512 will absorb charge fluctuations but keep the voltage generated by midrail reference 506 ($V_{mid}$) stable. This stability eases the design requirements on $V_{mid,ref}$ 508, which only needs to be strong enough to initially charge up $C_{mid}$ 512. The resistance $R_{mid}$ 510 also enhances safety by limiting any faulty DC current that may attempt to return to ground through $V_{mid, ref}$ 508.

Figure 10:
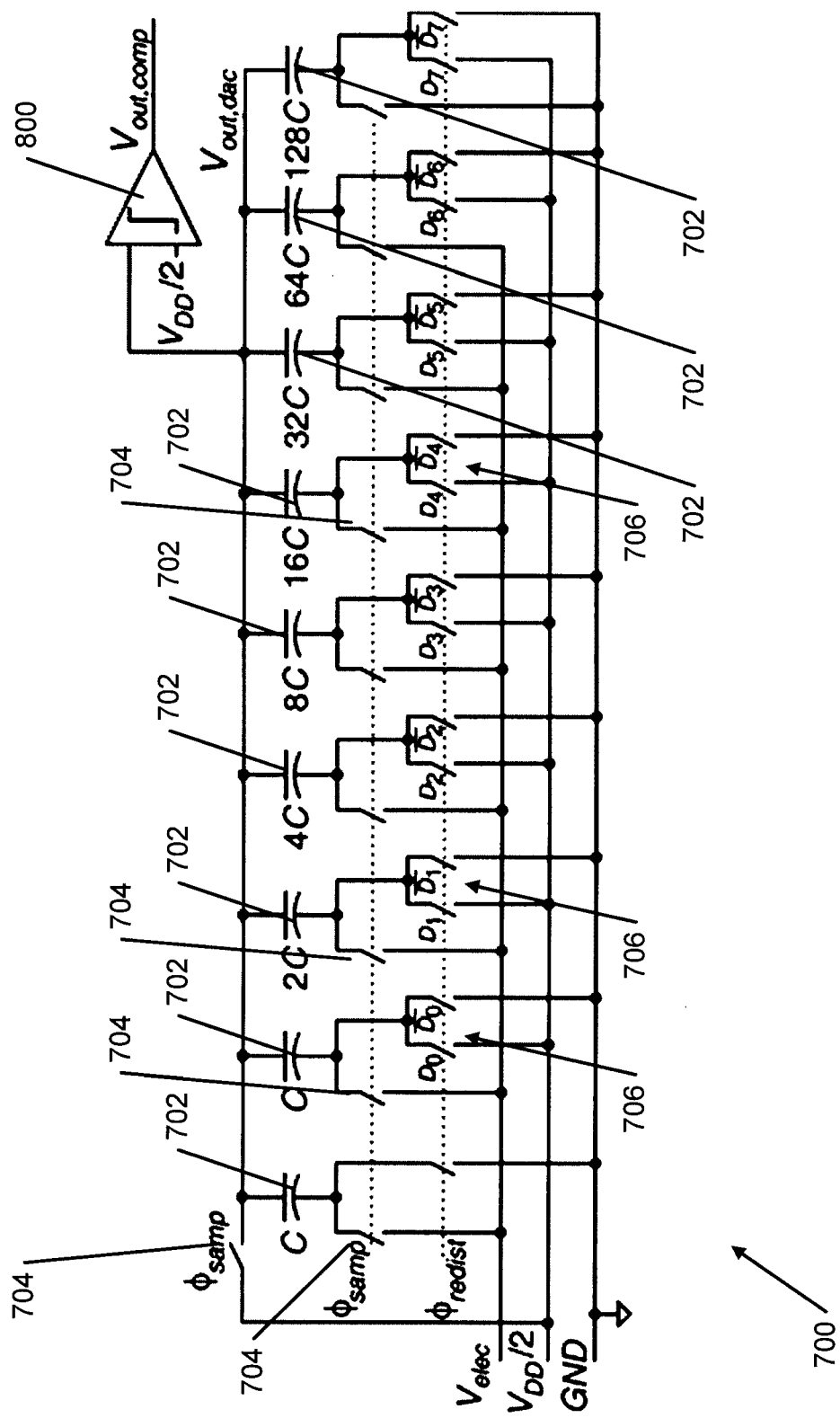

FIG. 10 is a schematic showing one example implementation of a DAC that may be used in implementing DAC and comparator 314 of FIG. 5a. The DAC operates in conjunction with a comparator (e.g., the comparator shown in FIG. 12) to compare a measured voltage (e.g., $V_{elec}$ of FIG. 5a) to a reference voltage (e.g., set voltage 316 of FIG. 5a). In this implementation, DAC 700 is a charge redistribution DAC that works in conjunction with a comparator to measure the electrode voltage $V_{elec}$, and compare the electrode voltage to a reference voltage that can be set digitally via bits $D_0$-$D_7$. In other implementations, other DAC and comparator configurations can be used to compare the measured voltage with the set or reference voltage. For example, DACs such as pipeline, successive approximation, or binary-weighted DACs could be used in conjunction with existing comparators to implement the functionality of DAC 700 and associated comparator 800. Even so, DAC 700 illustrated in FIG. 10 is more energy efficient than many other conventional DACs.

DAC 700 and comparator 800 (FIG. 12) operate on multiple phases that are controlled, for example, by controller 10 of FIG. 1. During a first phase of DAC 700 operation $\phi_{samp}$, $V_{elec}$ (the voltage across the electrode—see FIG. 5a) is sampled onto the capacitor array 702 of DAC 700. During a second phase of operation ($\phi_{redist}$), charge is redistributed within the capacitor array based on the value of the inputted digital value (i.e., bits $D_0$-$D_7$) to determine a difference between $V_{elec}$ and the set voltage. The phases $\phi_{samp}$ and $\phi_{redist}$ are non-overlapping. For reference, the DAC phases are indicated in parenthesis in FIG. 11 with the phases of operation of comparator 800.

DAC 700 is illustrated in FIG. 10 using a normalized capacitor unit C. In one example implementation, though, C has a value of 24 fF. In analyzing the operation of DAC 700 below, a corresponding normalized charge unit, denoted by Q', is used (this normalized charge unit presumes that all unit capacitors are equal to 1 and unitless).

During the sample phase, the switches controlled by $\phi_{samp}$ close (i.e., switches 704), connecting the top plate of each capacitor in DAC 700 to $V_{DD}/2$ and every bottom plate, except that of the rightmost capacitor (the MSB capacitor), to $V_{elec}$, the voltage across the electrode (see FIG. 5a). The MSB capacitor (128C) is instead connected to ground. Since the weight of the MSB capacitor, 128, is equal to the weights of the other capacitors combined, this has the effect of sampling half of the electrode voltage $V_{elec}$ onto the capacitor array. As such, although the electrode voltage may be rail-to-rail (ground to $V_{DD}$), the internal reference voltages of the DAC and comparator can be at $V_{DD}/2$.

Thus, the normalized charge sampled on to the capacitor array is given by Equation 7.

$$Q' = \left(\frac{V_{DD}}{2} - V_{elec}\right) \times 128 + \left(\frac{V_{DD}}{2} - 0\right) \times 128 = (V_{DD} - V_{elec}) \times 128 \quad (6)$$

At the end of $\phi_{samp}$, the top plate switch opens, locking in the charge onto the capacitor array. Later, the bottom plate sampling switches 704 open.

During the redistribution phase, $\phi_{redist}$, each capacitor's bottom plate will be connected to either $V_{DD}/2$ or GND, depending on the DAC set voltage code represented by individual bits $D_i$ of the set voltage value. This scheme is shown in FIG. 10 as a pair of switches 706 per capacitor, each controlled by $\phi_{redist}$ and the state of $D_i$, where i is the i th bit of the set voltage value (see set voltage 316 of FIG. 5a). Accordingly, in an 8-bit implementation the set voltage code is an integer having a value between 0 and 255 inclusive. Again, any number of bits in the set voltage value can be used in accordance with system requirements. In that case, a corresponding number of capacitors having capacitances 1C, 2C, 4C, 8C, . . . , $2^n$C, etc. can be used in the DAC.

At this point, $V_{out,dac}$, the output voltage of DAC 700 remains unknown. The charge stored by the capacitors whose bit $D_i$ was high is therefore:

$$\left(V_{out,dac} - \frac{V_{DD}}{2}\right) \times \text{code}. \quad (7)$$

The charge stored by the capacitors whose bit $D_i$ was low, including the leftmost capacitor, which is connected to GND during the redistribution phase, is:

$$(V_{out,dac} - 0)(256 - \text{code}) \quad (8).$$

These equations lead to a total charge stored on the entire array, following redistribution:

$$Q' = \left(V_{out,dac} - \frac{V_{DD}}{2}\right) \times \text{code} + (V_{out,dac} - 0)(256 - \text{code}) \quad (9)$$
$$= -\frac{V_{DD}}{2} \times \text{code} + V_{out,dac} \times 256$$

Since charge is conserved between the sampling and redistribution phases, Equations 6 and 9 can be equated to solve for $V_{out,dac}$ after redistribution.

$$-\frac{V_{DD}}{2} \times \text{code} + V_{out,dac} \times 256 = (V_{DD} - V_{elec}) \times 128; \quad (10)$$

which simplifies to:

$$\boxed{V_{out,dac} = \frac{V_{DD}}{2} - \left(\frac{V_{elec}}{2} - \left(\frac{V_{DD}}{2} \times \frac{\text{code}}{256}\right)\right).} \quad (11)$$

Thus, $V_{out,dac}$ is equal to $V_{DD}/2$ only if $V_{elec}=V_{DD}\times\text{code}/256$. Accordingly, if $V_{elec}$ is equal to the voltage identified by the set voltage value, the output of DAC 700 ($V_{out,dac}$) equals $V_{DD}/2$. If the two values differ, though, the output of DAC 700 ($V_{out,dac}$) diverges from $V_{DD}/2$. If, for example, $V_{elec}$ is less than the set voltage, the output of DAC 700 is greater than $V_{DD}/2$. Conversely, if $V_{elec}$ is greater than the set voltage, the output of DAC 700 is less than $V_{DD}/2$.

The voltage $V_{out,dac}$ is directly connected to clocked comparator 800, the output of which, $V_{out,comp}$, is also shown in FIG. 10. Comparator 800 compares $V_{out,dac}$ to $V_{DD}/2$ and generates an output that is affected by whether comparator 800 is operating in stimulating down-conversion mode or recycling up-conversion mode. If comparator 800 is in stimulating down-conversion mode and $V_{out,dac}$ is greater than $V_{DD}/2$, the output of comparator 800 is high, indicating that $V_{elec}$ is less than the set voltage. In that case, as described above, the pulse generator (e.g., pulse generator 600 of FIG. 8) receives the high value from comparator 800 and initiates a pulse sequence causing the stimulator core (e.g., core 310 of FIG. 5*a*) to deliver more energy to the electrode. Conversely, if comparator 800 is in stimulating down-conversion mode and $V_{out,dac}$ is less than $V_{DD}/2$, the output of out, comparator 800 is low, indicating that $V_{elec}$ is greater than the set voltage. In that case, as described above the pulse generator (e.g., pulse generator 600 of FIG. 8) receives the low value from comparator 800 and takes no action. When in recycling up-conversion mode, the output of comparator 800 is reversed.

Depending upon the system implementation, the current operational mode of the stimulator (e.g., the STIM/REC value shown in FIG. 5*a*) may be inputted into a circuit coupled to the output of comparator 800 to cause the output of comparator 800 to be inverted when the system is in recycling up-conversion mode.

In accordance with the present disclosure, other comparator systems could be used to compare the difference received from DAC 700 to a reference value and transmit an indication of any such difference to the pulse generator. Other conventional comparators or analog-to-digital converters coupled with appropriate logic, for example, can be used in place of comparator 800 to achieve the functionality described above.

Figure 11:
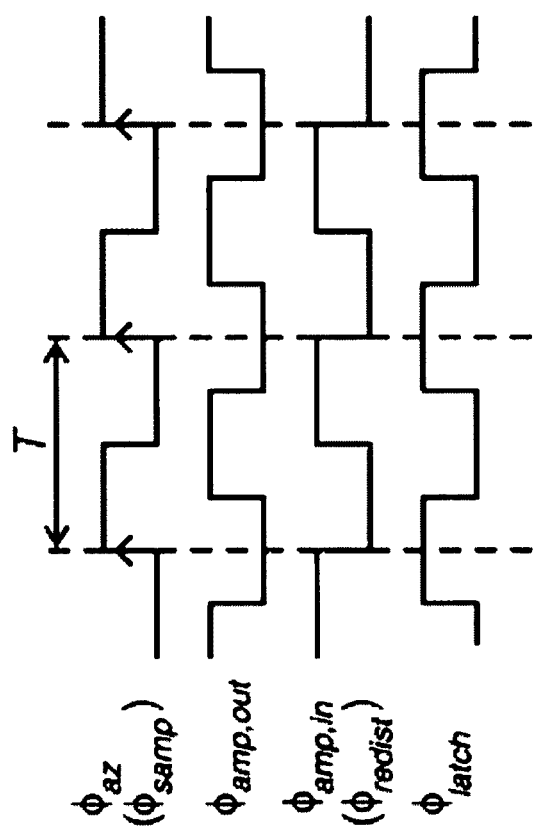
FIG. 11 is a timing diagram illustrating a sequence of state phases that may be processed by a DAC and comparator implemented in accordance with the present disclosure.
Figure 12:
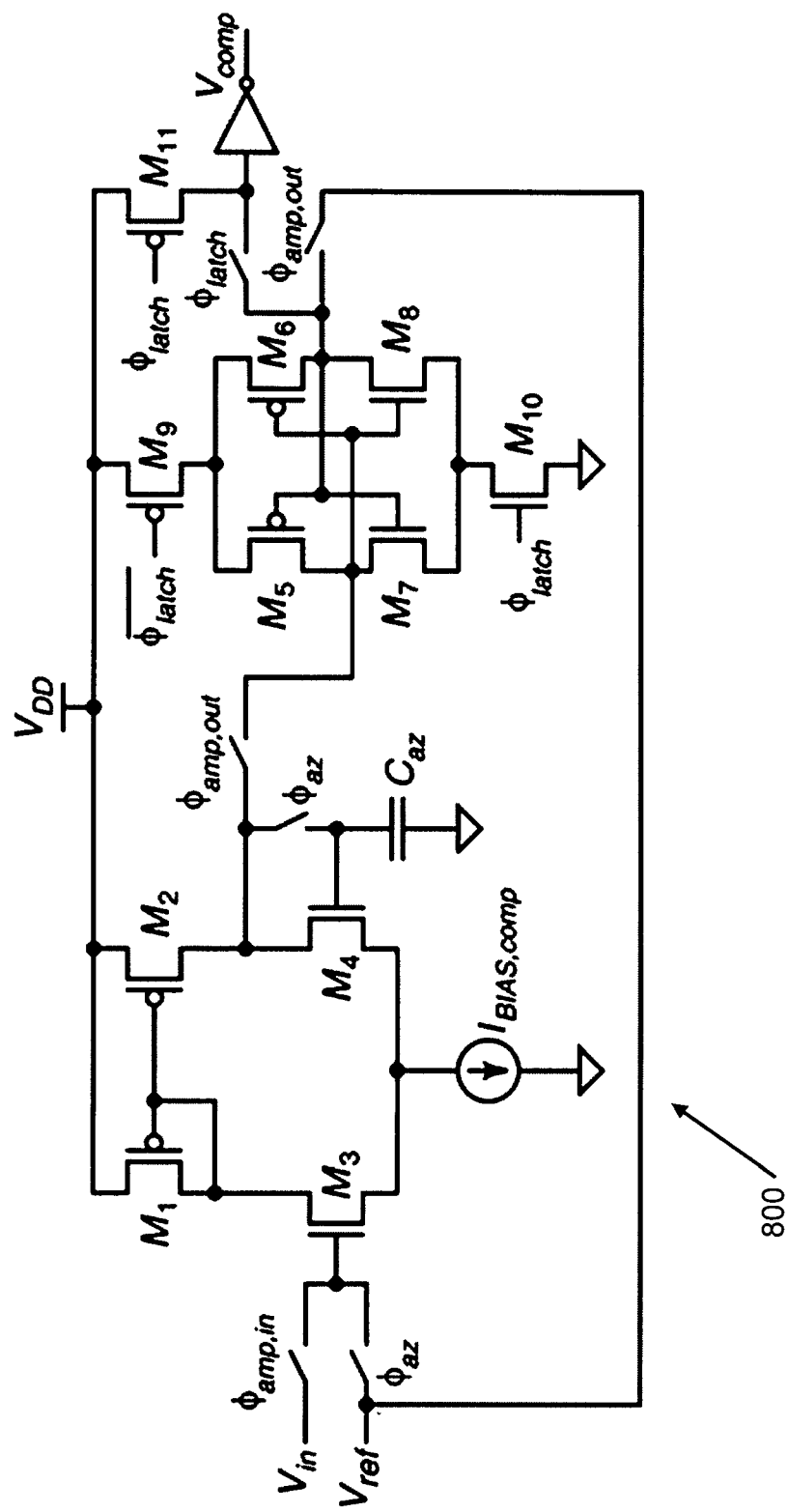
FIG. 12 is a schematic diagram of an example comparator that may be used in conjunction with DAC 700 illustrated in FIG. 10.

FIG. 12 is an illustration of an example comparator that may be used in conjunction with DAC 700 illustrated in FIG. 10. The comparator can be operated using a series of four overlapping phases ordered as shown in FIG. 11. The comparator phases coincide with the sampling and redistribution of the phases of the DAC, as described above. In one implementation, the comparator uses a clocked design, consisting of a preamplifier (including switches $M_1$-$M_4$), and a latch (including switches $M_5$-$M_8$).

The operation of comparator 800 is as follows: During the $\phi_{az}$ phase, the preamplifier is placed in unity-gain. The input to the preamplifier is $V_{ref}$ (equal to $V_{DD}/2$). Thus, because of the unity gain configuration, the output of the preamplifier is also $V_{ref}$, excluding any offset that may exist within the preamplifier and any errors due to the amplifier's finite DC gain. The overall topology results in the preamplifier being auto-zeroed, with any offset stored on $C_{az}$. Approximately halfway through the $\phi_{az}$ phase, the comparator enters $\phi_{amp,out}$, which connects the output of the preamplifier to the output of the latch which is, for the moment, in a high-impedance or "high-Z" state because $\phi_{latch}$ and $\overline{\phi_{latch}}$ are in an inactivating state for $M_{10}$ and $M_9$. The complementary output of the latch, also high-Z, is held at $V_{ref}$. Note that if the preamplifier were fully differential, the complementary output of the latch would receive the corresponding complementary output of the differential preamplifier. Making the preamplifier output single-ended simplifies the comparator design. In principle, the output of the preamplifier does not move during this transition because the preamplifier input has not changed and the offset value is still held on $C_{az}$. Approximately halfway through $\phi_{amp,out}$, $\phi_{az}$ ends and $\phi_{amp,in}$ begins. At the same time, the DAC transitions from the sampling phase ($\phi_{samp}$) to the redistribution phase ($\phi_{redist}$). The DAC output, which is now valid, is connected to the input of the preamplifier ($V_{in}$). Any difference between and $V_{in}$ and $V_{ref}$ is amplified. Approximately halfway through $\phi_{amp,in}$, $\phi_{amp,out}$ ends, locking the preamplified value in on the latch's own parasitic capacitance. Simultaneously, $\phi_{latch}$ begins, which causes the latch to regenerate. During $\phi_{latch}$ when comparator 800 is operating in stimulating down-conversion mode, the output $V_{comp}$ is high when $V_{in} > V_{ref}$ and low when $V_{in} < V_{ref}$. At other times, $V_{comp}$ is low due to the action of $M_{11}$. Conversely, when in recycling up-conversion mode, the output $V_{comp}$ is low when $V_{in} > V_{ref}$ and high when $V_{in} < V_{ref}$.

To regulate the flow of current to and from the electrode, a circuit (see, for example, current sensor 320 of FIG. 5*a*) for sensing the current in the electrode is used. One possible design of the current sensor is to use a small series resistor to convert current into voltage, which can then be measured. This method has two disadvantages though—the use of a series sense resistor reduces valuable voltage headroom, and also consumes power. The larger the sense resistor, the worse each of these two problems become. Further, a small sense resistor produces only small voltages, for instance, 1-10 mV for a 10Ω resistor carrying 100-1000 μA of current. To be useful, these voltages would need to be amplified by an AC coupled or offset-compensated amplifier to avoid large output offsets drowning the small sense signal.

An alternative design approach measures changes in the capacitor voltage $V_{out}$ over a fixed time caused by the electrode current discharging the capacitor $C_{out}$ (see, for example, capacitor 408 of FIG. 6*a*). To ensure that the voltage change are solely caused by the electrode current, switches $M_p$ and $M_n$ (see switches 402 and 404 of FIG. 6*a*) are held in an open position during this measurement phase such that the current to the electrode is supplied from $C_{out}$. If $C_{dl} \gg C_{out}$, which is often the case, and $R_s C_{out} \gg T$, where T is the adaptive voltage stimulator switching period, current leaks from $C_{out}$ at an approximately constant rate, resulting in a linear droop in the voltage on $C_{out}$. If the change in the electrode voltage $\Delta V_{elec}$ is measured during a sense interval $T_{sense}$, the electrode current I is approximately given by:

$$I = C_{out} \frac{\Delta V_{elec}}{T_{sense}}. \qquad (12)$$

Symmetric measurements occur during charging or discharging of $C_{out}$ depending on the sign of the electrode current.

Figure 13:
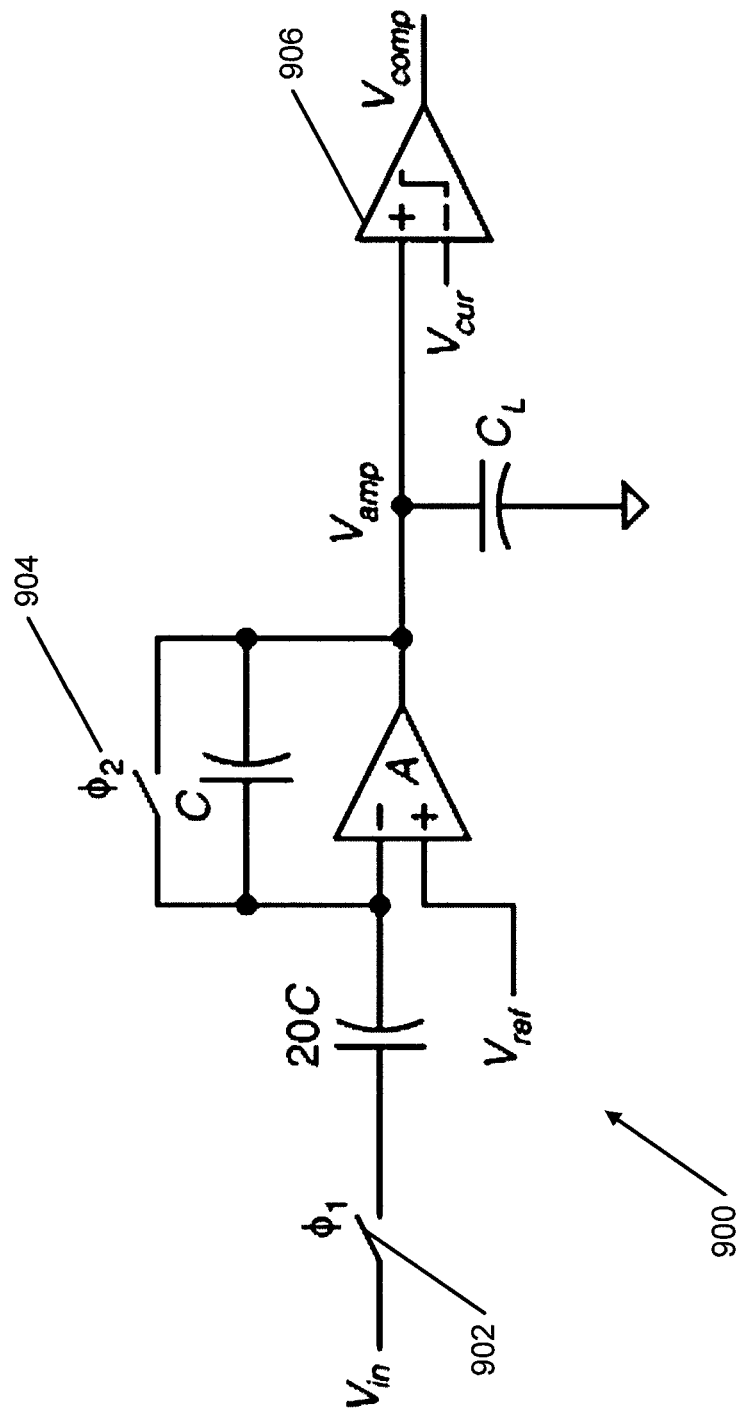
FIG. 13 is a schematic diagram of one implementation of a current sensor, such as current sensor 320 of FIG. 5a, that may be used in conjunction with the present electrode stimulator.
Figure 14:
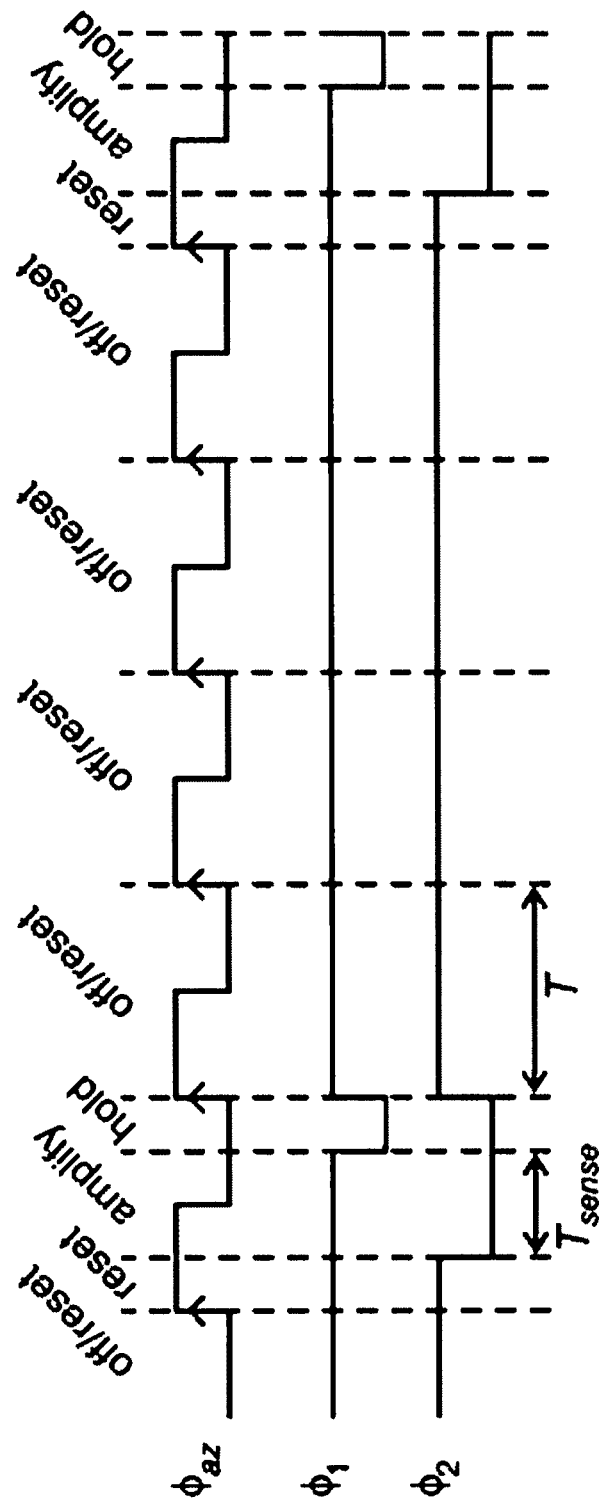
FIG. 14 is a timing diagram illustrating a sequence of state phases that may be processed by a current sensor implemented in accordance with the present disclosure.

FIG. 13 illustrates one implementation of current sensor 900 such as current sensor 320 of FIG. 5*a*. The current-sensor circuit shown in FIG. 13 is configured to measure $\Delta V_{elec}$. The circuit draws little power from the electrode, and because the circuit is in a shunt configuration with the electrode rather than in series with the electrode, the electrode's voltage headroom is unaffected. The current-sensor circuit operates as a hybrid of a conventional capacitive-feedback amplifier and a track-and-hold circuit. The circuit has 3 primary phases of operation controlled by the states of two switches, themselves controlled by the signals $\phi_1$ and $\phi_2$. FIG. 14 illustrates the phase timing for each phase of operation for the current sensor.

The operation of the current-sensor circuit is as follows: When both $\phi_1$ and $\phi_2$ are high, both switches $\phi_1$ (902) and $\phi_2$ (904) in FIG. 13 are closed, corresponding to a reset phase of current sensor. The amplifier runs in unity gain, high-pass filtering the input. The DC level of $V_{amp}$ settles to $V_{ref}$. During this time switches 402 ($M_p$) and 404 ($M_n$) of the adaptive voltage stimulator (see, for example, FIG. 6a) may be active causing energy to be either delivered to or removed from the electrode. Next, the switch controlled by $\phi_2$ (904) opens for a period of $T_{sense}$, placing the amplifier into a gain configuration whereby any changes in $V_{in}$ are inverted and amplified by the gain determined by capacitor ratio, i.e., by a gain of minus 20. During $T_{sense}$, both switches 402 ($M_p$) and 404 ($M_n$) of the adaptive voltage stimulator (see, for example, FIG. 6a) are open, isolating the electrode from any external power source or sink. Finally, after the interval $T_{sense}$ elapses, the switch controlled by $\phi_1$ (902) opens as well. With the input disconnected, $V_{amp}$ is held by the amplifier while $V_{amp}$ is compared to the reference voltage $V_{cur}$. Thus, the relationship between $V_{amp}$ and $V_{cur}$ indicates whether the measured current was above or below the set value. In the recycling up-conversion mode, $\Delta V_{elec}$ has the opposite sign compared to the stimulating down-conversion mode because the load powers $C_{out}$, causing $V_{elec}$ to rise linearly instead of fall. Therefore, the output of comparator 906 is high when $V_{amp}$ is greater than $V_{cur}$ and low when $V_{amp}$ is less than $V_{cur}$. In both cases, $|V_{cur}-V_{ref}|$ encodes a desired current magnitude in the slow current loop. The output from comparator 906 is provided to a counter (see, for example, counter 322 of FIG. 5a) where the signal is used to either increment, or decrement the set voltage value depending upon operational mode, as described above. In some implementations, though, the output from comparator 906 is inverted in the recycling up-conversion mode such that the sign of the up/down error correction in the feedback loop shown in FIG. 5a is automatically correct, in which case the counter does not change its behavior based upon operational mode.

FIG. 14 is a timing diagram illustrating the temporal relationship between the various phases of operation of current sensor 900. As can be seen in FIG. 14, the current-sensor circuit only detects and generates an output once in every five conversion cycles of the adaptive voltage stimulator. This strategy allows ample settling time for the adaptive voltage stimulator to reach its new set point and helps to ensure stability of $V_{out}$.

An important characteristic of stimulators, which can be calculated even if the properties of the electrode are unknown, is the ratio of the energy consumed by the stimulator to the energy that a constant current source stimulator would have used. This ratio is defined to be the Energy Factor relative to a constant Current Source stimulator ($EF_{CS}$). The minimum possible $EF_{CS}$ is electrode dependent. An $EF_{CS}$ less than 1 indicates a performance improvement with respect to a current source stimulator while an $EF_{CS}$ greater than 1 indicates that a constant current source would be more energy efficient.

During stimulation, because the electrode's return is at $V_{mid}$ and not at ground, there may be energy stored in $C_{mid}$ during stimulation. This may be true whether or not the mid-rail reference is generated as shown in FIG. 7 (see element 506), or if an explicit voltage source is used instead. Either way, the voltage $V_{mid}$ is assumed to be constant throughout the duration of a stimulation. This assumption may be accurate if $C_{mid}$ is large enough and as long as current stimuli are charge-balanced.

Figure 15:
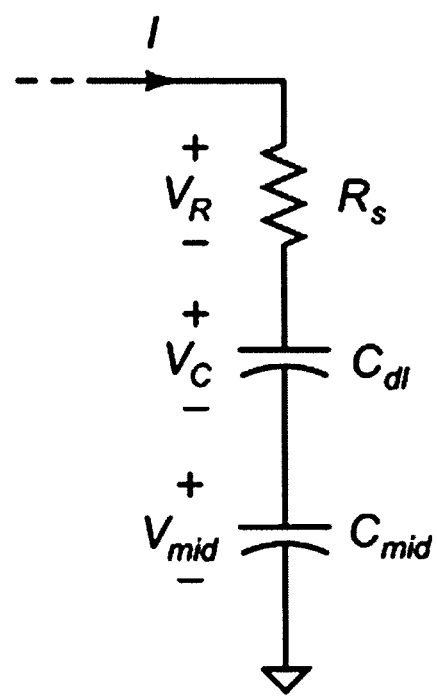
FIG. 15 is a schematic diagram of an example model of an electrode including a resistance and capacitance connected in series with a model capacitance of a voltage reference.

From FIG. 7, it is apparent that the electrode's resistance $R_s$ and capacitance $C_{d1}$ is in series with $C_{mid}$, as shown in FIG. 15. As such, when the electrode is charged with a constant current $I_{stim}$ for duration $T_{stim}$, the energy stored in the electrode capacitance is $$E_C = \frac{1}{2}C_{dl}V_C^2.$$

The energy stored in the midrail capacitor $C_{mid}$ is a $E_{mid}=V_{mid} \times I_{stim} \times T_{stim}$, where $C_{mid}$ is large enough to behave as a power supply for small signals. Therefore, the total energy stored in both the electrode and in $C_{mid}$ is:

$$E'_C = \left(\frac{1}{2} + V_{mid}\right) \times I_{stim} \times T_{stim}. \tag{13}$$

If $V_{mid}$ is equal to $V_{DD}/2$, the ratio of the energy stored in $C_{mid}$ to the energy stored in the electrode capacitance is $V_{DD}/V_C$. Thus, during a stimulation, the peak energy stored in $C_{mid}$ may be several times that stored in $C_{d1}$. In principle, the only energy required to be transferred is that which will be stored in $C_{d1}$, plus any energy dissipated in $R_s$. An adaptive voltage stimulator with perfect efficiency suffers no consequences from transferring energy back and forth. However, transferring extra energy, although it can be recovered during the second, charge-balancing phase of the stimulation, is dissipative because of adaptive voltage stimulator losses—no inductors, capacitors, or switches are perfectly lossless.

A current-source-based stimulator is configured to consume the same amount of energy, given by $E_{CS}=V_{DD} \times I_{stim} \times T_{stim}$, regardless of the electrode impedance. Note that in FIG. 2b, the current-source stimulation stores energy in $V_{mid}$ during a charging phase when $I_{CS,P}$ is on, but dissipates that stored energy during a discharging phase when $I_{CS,N}$ is on. The net energy dissipation over both phases is given by:

$$((V_{DD}-V_{mid})I_{stim}+V_{mid} \times I_{stim})T_{stim}$$

$$=V_{DD} \times I_{stim} \times T_{stim} = E_{CS} \tag{14}.$$

In both current source stimulators and in the present stimulator, if $V_{mid}=V_{DD}/2$, a peak energy $E_{mid,pk}=E_{CS}/2$ is stored on $C_{mid}$ during the transition between charging and discharging phases. To supply $E_{mid,pk}$, an energy $E_{mid,pk}/\eta$ would be taken from $V_{DD}$, and an amount $E_{mid,pk} \times \eta$ would be returned. Compared to the energy consumed in a constant current source design, $E_{CS}=2E_{mid,pk}$, the following is obtained:

$$EF_{CS} \geq \frac{1-\eta^2}{2\eta}. \tag{15}$$

Thus, implementations of the present stimulator system perform at the same level as a constant current source stimulator when $\eta=\sqrt{2}-1=41.4\%$ Efficiencies of at least 75% are routinely achievable, giving the present stimulator an expected $EF_{CS}$ in some implementations of at least 0.29, or a 3.5× improvement over the constant current source stimulator for ideal electrodes.

Electrode resistance contributes electrode-dependent loss. The electrode capacitance also contributes loss because the capacitor must be charged and then discharged (or discharged and then charged) by a non-ideal adaptive voltage stimulator with less than 100% efficiency. The shuttling of electrode capacitive energy is subject to the imperfect efficiency of the adaptive voltage stimulator, just as is the energy stored in the midrail, $E_{mid}$.

To calculate $EF_{CS}$ for an electrode with resistance $R_s$ and capacitance $C_{dl}$, the voltage drop, $V_R$, across the electrode resistance during the stimulation, and the peak voltage attained across the electrode capacitor, $V_C$, are to be known. It is useful to express both voltages as a fraction of the midrail voltage. Therefore, $\alpha_C$ and $\alpha_R$ are defined such that $V_C = \alpha_C V_{mid}$, and $V_R = \alpha_R V_{mid}$. For simplicity, it can be assumed that the electrode receives positive constant current during the first stimulation phase, and negative constant current during the second stimulation phase. However, the calculation has identical results even if the phase order is reversed. Thus, during the first phase of an electrode stimulation, if the energy stored in the midrail supply is $E_{mid}$, then the energy stored in the electrode capacitance is $(\alpha_C/2)E_{mid}$ because the average voltage across $C_{dl}$ during charging is $V_c/2 = (\alpha_C/2)V_{mid}$. Finally, the energy dissipated in the resistor is $\alpha_R E_{mid}$. The sum of these three component energies is divided by $\eta$ to determine the amount of energy that must have been taken from $V_{DD}$. During the second phase, energy is recovered from both the midrail supply and the electrode capacitor, but is dissipated in the electrode resistor. This energy is subject to the adaptive voltage stimulator efficiency, reducing the amount that can be returned to $V_{DD}$. Referring to the net energy taken from the supply as $E_{sup}$, the general form of $EF_{CS}$ that includes all losses is given by:

$$EF_{CS} = \frac{E_{sup}}{E_{CS}} = \frac{\left(E_{mid} + \frac{1}{2}\alpha_C E_{mid} + \alpha_R E_{mid}\right)\frac{1}{\eta}}{2E_{mid}} - \frac{\left(E_{mid} + \frac{1}{2}\alpha_C E_{mid} - \alpha_R E_{mid}\right)\eta}{2E_{mid}} = \frac{1-\eta^2}{2\eta}\left[1 + \frac{\alpha_C}{2} + \alpha_R \frac{(1+\eta^2)}{(1-\eta^2)}\right]. \quad (16)$$

Note that Equation 16 is consistent with the minimum value of $EF_{CS}$ predicted by Equation 15 that analyzed $EF_{CS}$ when there is no loss in the electrode.

Figure 16:
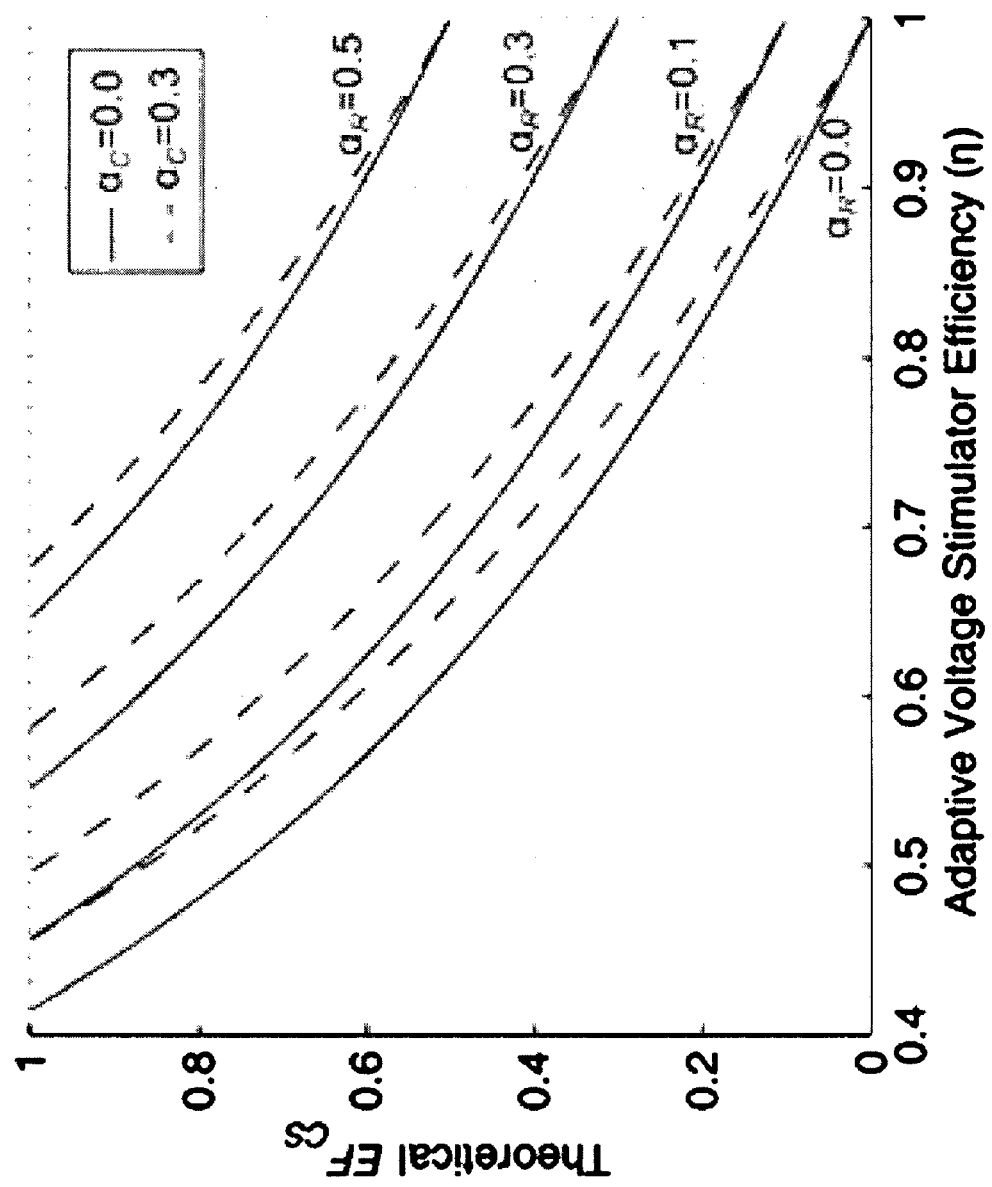
FIG. 16 is a plot of the theoretical efficiency of one implementation of the present stimulator device versus $\eta$ for various values of $\alpha_C$ and $\alpha_R$ according to Equation 15.

FIG. 16 is a plot of the theoretical $EF_{CS}$ versus $\eta$ for various values of $\alpha_C$ and $\alpha_R$ according to Equation 15. As expected, higher adaptive voltage stimulator efficiencies lead to a lower $EF_{CS}$ since energy recycling is then very efficient such that operation with respect to a constant current source stimulation is highly beneficial. At 90% adaptive voltage stimulator efficiencies, a 10× reduction in energy dissipation can be achieved. FIG. 16 also shows that as $\alpha_C$, and especially $\alpha_R$ increase, the $EF_{CS}$ rises because more electrode energy is lost due to imperfect energy recycling in the adaptive voltage stimulator. Nevertheless, for almost all practical values of $\alpha_R$, $\alpha_C$, and $\eta$, $EF_{CS}$ is well below 1.

Figure 17A:
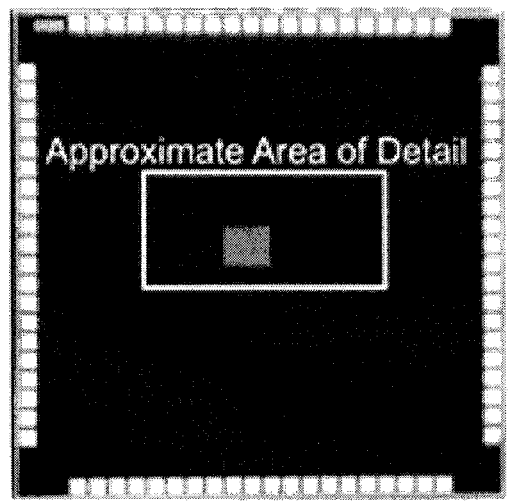
FIG. 17a is a microphotograph of a die containing an electronic circuit implementing the electrode stimulator of the present disclosure.
Figure 17B:
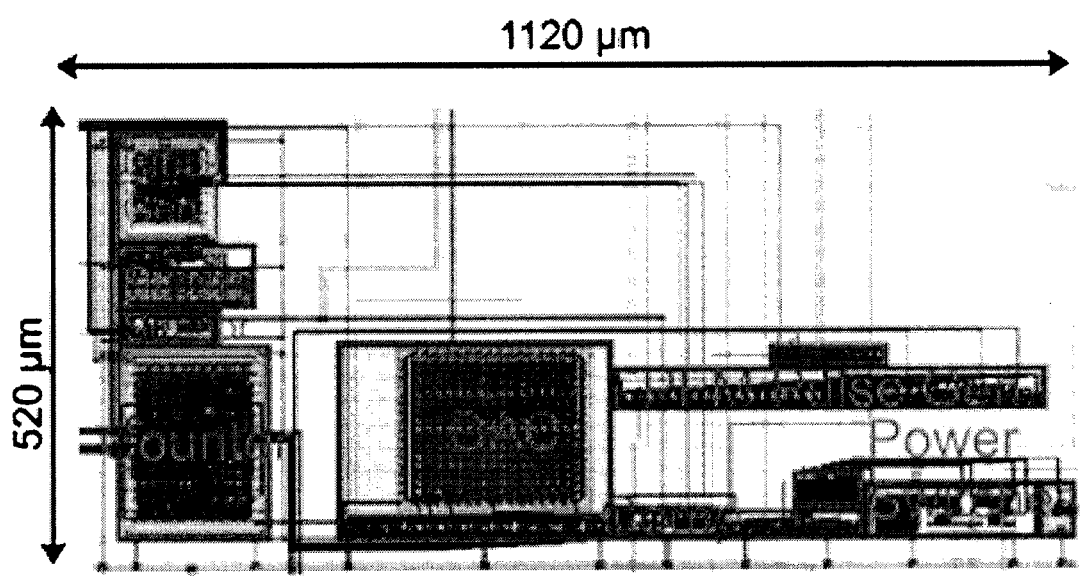
FIG. 17b is a layout of a die structure containing an electronic circuit implementing the electrode stimulator of the present disclosure.

In one implementation of the present system, a single stimulator channel was fabricated in the ON Semiconductor (formerly AMI) 0.35 μm CMOS process. A photograph of the die is shown in FIG. 17a and the layout of a single channel with key parts identified is shown in FIG. 17b. The stimulator was constructed with external components L=39 μH, $C_{out}$=47 nF, and $C_{in}$=4.7 μF. The period T for the voltage control was 4 μs (e.g., inner loop 302 of FIG. 5a), while the current control loop (e.g., outer loop 304 of FIG. 5a) sampled the current at 20 μs intervals.

Figure 18:
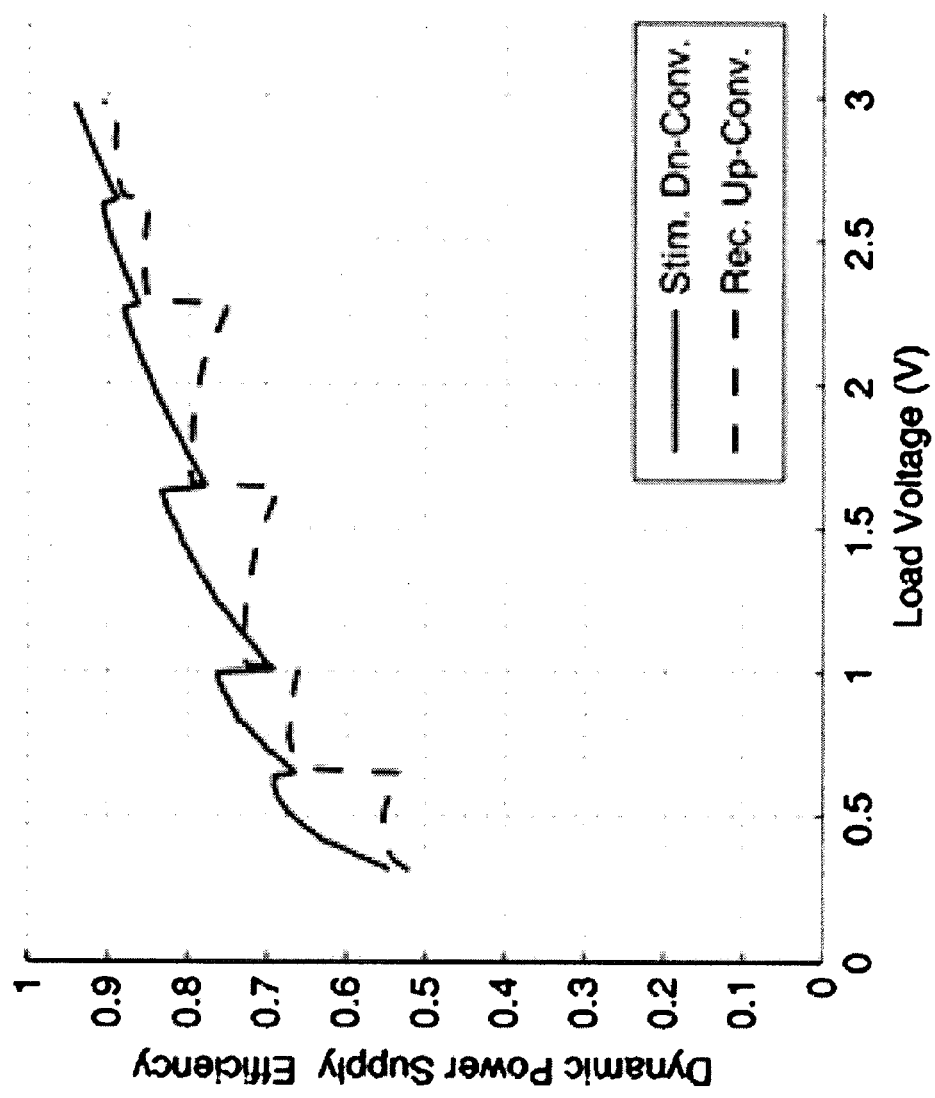
FIG. 18 is a graph illustrating the raw efficiency of one implementation of the present adaptive voltage stimulator when powering a 300 µA DC load.

FIG. 18 is a graph illustrating the raw efficiency of one implementation of the present adaptive voltage stimulator when powering a 300 μA DC load. This efficiency considers only the fundamental transfer of energy to and from $V_{DD}$ and the load via the adaptive voltage stimulator core, which effectively operates like a DC-DC converter. For these measurements, a fixed load was supplied by a DC current source. The output set voltage (e.g., element 316 in FIG. 5a) was swept over its entire range and measurements of the current from $V_{DD}$ and the output voltage were taken to obtain the DC-DC converter efficiency. Note that the slow current feedback loop (e.g., outer loop 304 of FIG. 5a) is effectively inactivated during these measurements because the set voltage is fixed externally and not allowed to vary. Although the current control loop was effectively overridden, it was not actually disabled. This procedure was repeated for both the stimulating and recycling adaptive voltage stimulator modes by exchanging the $V_{DD}$ input and $V_{elec}$ output. The output filter capacitor $C_{out}$ was chosen to be 1 μF just for these measurements in order to create a well-smoothed voltage for $V_{elec}$. The control loop power, which includes circuitry for electrode voltage and current sensing, set voltage counter, $D_1$ and $D_2$ pulse generation, and gate drive for $M_p$ and $M_n$, was about 40 μW. This control power overhead may reduce the net efficiency of the converter on average by a few percent. The bias currents for the current-sensor circuitry are still included in this control power.

Figure 19A:
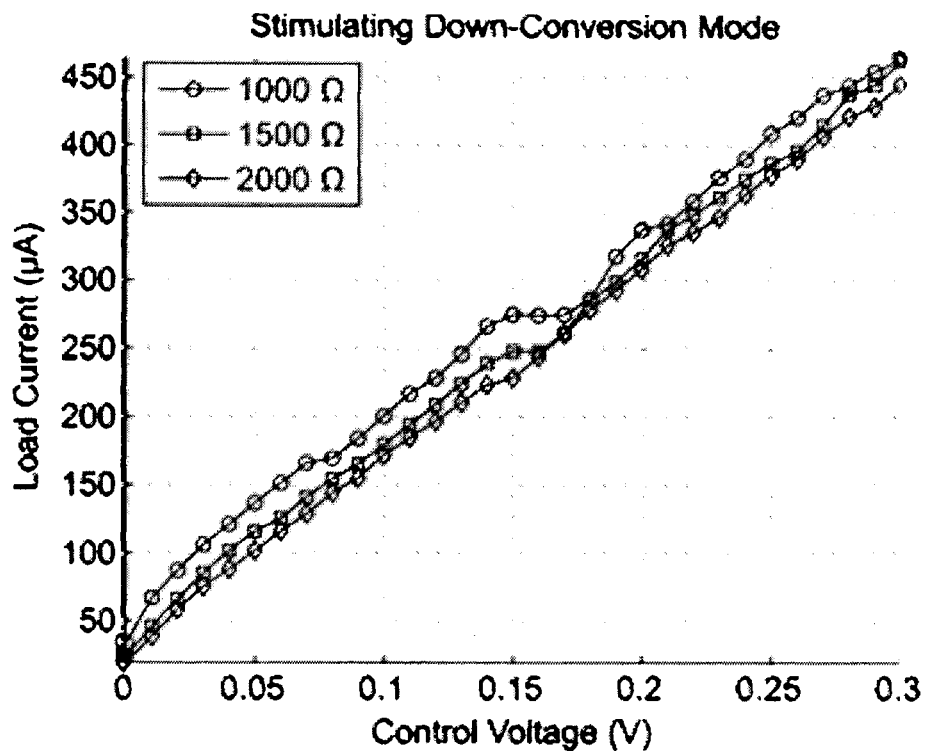
FIGS. 19a-19b are graphs illustrating load current versus control voltage for stimulating down-conversion mode (FIG. 19a), and recycling up-conversion mode (FIG. 19b) for different resistive loads.
Figure 19B:
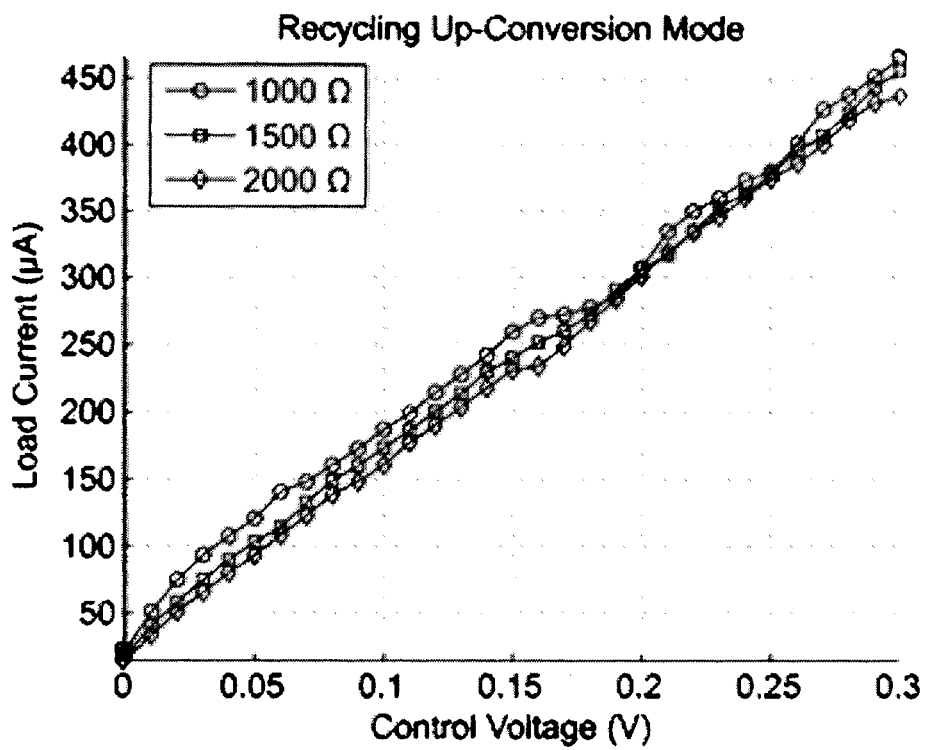

As described above, the current sensor/controller (e.g., current sensor 320 of FIG. 5a) of the present system operates by measuring the droop (stimulating down-conversion) or rise (recycling up-conversion) on $C_{out}$ in one conversion cycle to approximate the current. The rate of droop (or rise) is expected to be approximately invariant with load impedance, depending only on the load current. To characterize the current controller, the adaptive voltage stimulator was tested using different purely resistive loads. The data are shown in FIGS. 19a and 19b. The control voltage $V_{cur}$ was swept over a range of 0±300 mV about $V_{ref}$ to obtain data for the stimulating and recycling modes. As FIGS. 19a and 19b reveal, currents ranged from 0-450 μA with good linearity over the entire range. FIGS. 19a and 19b show that changes in load do not significantly affect the load current, as expected.

The stimulator was tested with several model loads consisting of a series resistor and capacitor. Two values of $V_{cur}$ were used, testing the stimulator at two different current levels. The values of the resistor and capacitor were chosen to be consistent with what is encountered with a Medtronic DBS electrode. The power supply voltage was 3.3 V. Stimuli were 2 ms in duration, with 1 ms/phase. The energy use of the stimulator was measured by monitoring the voltage on $C_{in}$ throughout the stimulation. Since energy recycling is not perfect, $C_{in}$ was periodically "topped off" to recharge it back to $V_{DD}$. The change in the voltage across $C_{in}$ during one stimulation represents the stimulator's energy usage.

Figure 20A:
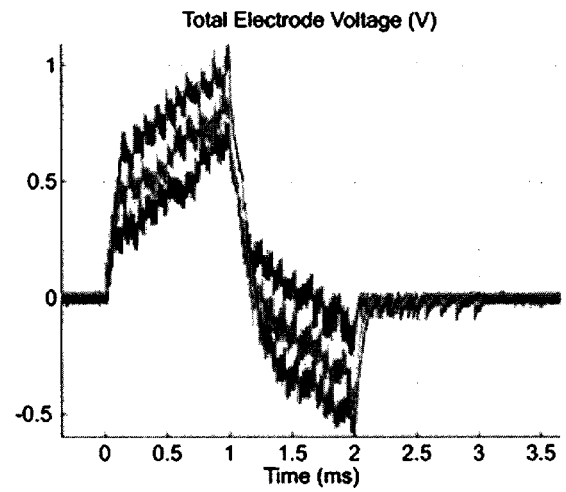
FIGS. 20a-20d are graphs illustrating example stimulator waveforms for $|V_{cur}-V_{ref}|=300$ mV, showing anodic-first electrode voltage (FIG. 20a), electrode current corresponding to FIG. 20a (FIG. 20b), cathodic-first electrode voltage (FIG. 20c), and electrode current corresponding to FIG. 20c (FIG. 20d).
Figure 20B:
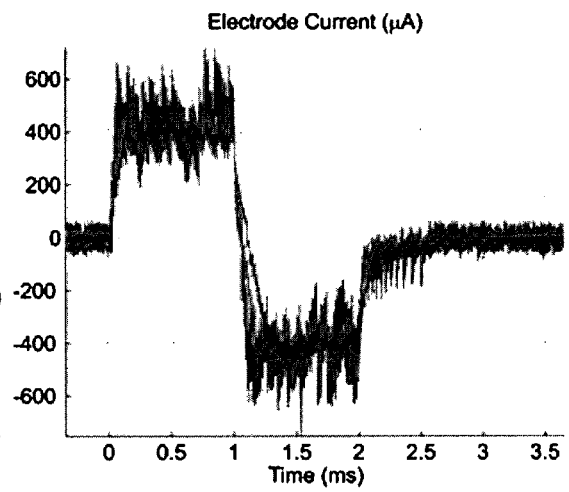
Figure 20C:
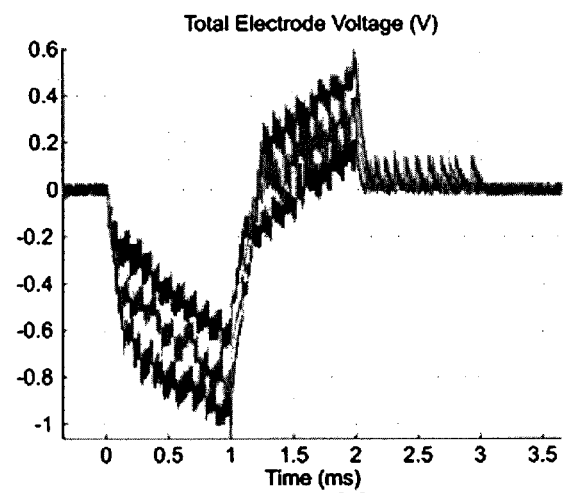
Figure 20D:
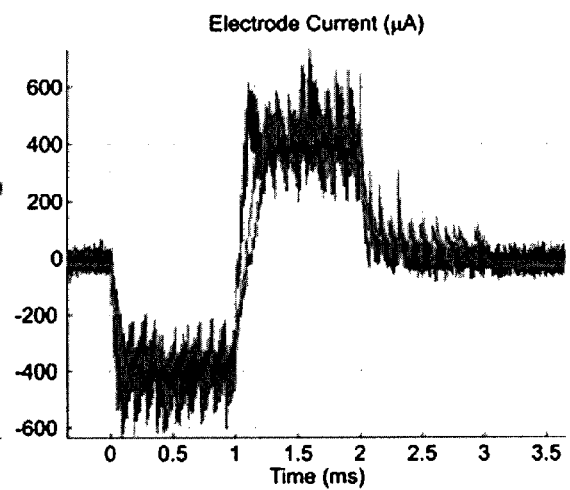

Examples of stimulator waveforms for $|V_{cur}-V_{ref}|=300$ mV are given in FIGS. 20a-20d. In FIGS. 20a and 20b, the voltage and current waveforms are shown for anodic-first stimuli. In FIGS. 20c and 20d, the same stimuli were applied cathodic first. The loads consist of a 0.93 μF capacitor in series with a 500, 1000 or 1500Ω resistor. As in FIGS. 19a and 19b, it can be seen in FIGS. 20a-20d that variations in load impedance do not significantly affect the load current due to regulation by the current feedback loop, even as the load voltage is continuously changing.

Figure 21A:
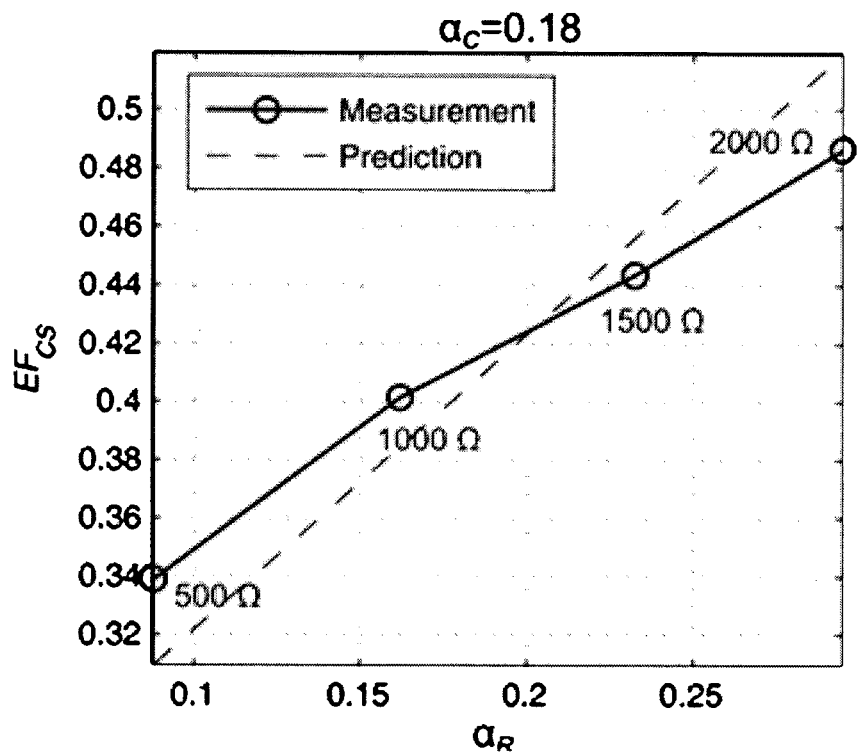
FIGS. 21a-21b are graphs illustrating average $EF_{CS}$ measurements where $|V_{cur}-V_{ref}|=200$ mV and theoretical predictions (FIG. 21a), and average $EF_{CS}$ measurements where $|V_{cur}-V_{ref}|=300$ mV and theoretical predictions (FIG. 21b).
Figure 21B:
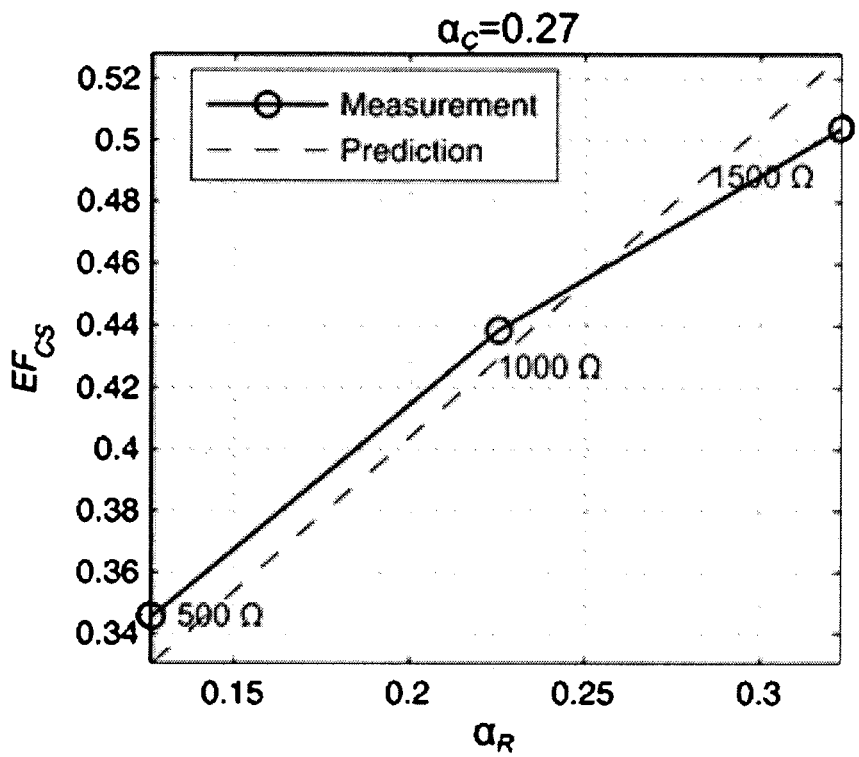

In FIGS. 21a-21b, the measured values of $EF_{CS}$ are shown. In FIG. 21a, $|V_{cur}-V_{ref}|=200$ mV. Since $C_{dl}$ was set constant at 0.93 μF, $\alpha_C$ is approximately 0.18 since $V_{cur}$ is not varied. However, different values for $R_s$ were selected, thus varying $\alpha_R$. Each value of $EF_{CS}$ was obtained by aggregating many trials with those particular values of $V_{cur}$, $C_{dl}$, and $R_s$. To see if the theory would agree with the data, the measured values of $\alpha_C$, $\alpha_R$, and $EF_{CS}$ were input into Equation 15 and a best-fit line was obtained by finding the value of $\eta$ that minimized the least-squared error. The values of $\eta$ obtained from the fit were 82% for $|V_{cur}-V_{ref}|=200$ mV and 84% for $|V_{cur}-V_{ref}|=300$ mV. Both values are quite reasonable considering the measured values of the adaptive voltage stimulator efficiency under DC conditions.

It should be noted that these measurements do not include the energy required to run the control loop during the stimulation. However, that penalty is small—approximately 12 μA of current from a 3.3 V supply during the stimulation.

Figure 22B:
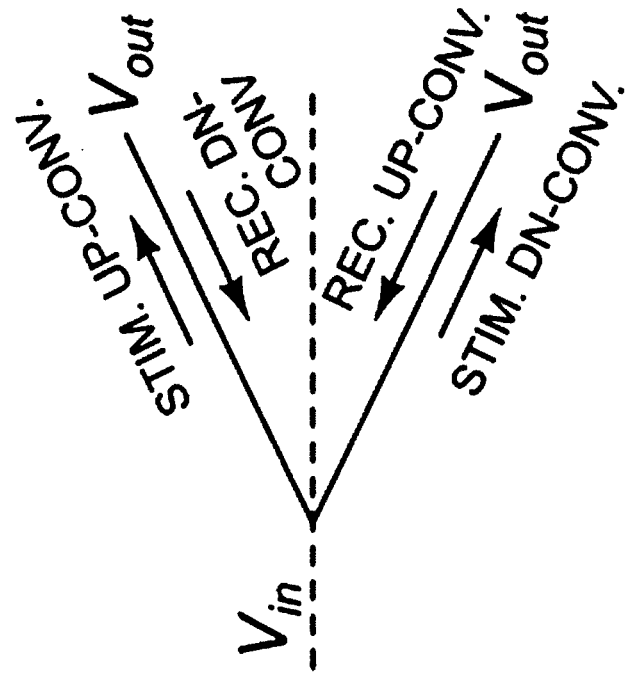
FIGS. 22a and 22b show ideal range output voltages and flow of power for a two-mode adaptive voltage stimulator (FIG. 22a) and a four-mode adaptive voltage stimulator (FIG. 22b).
Figure 22A:
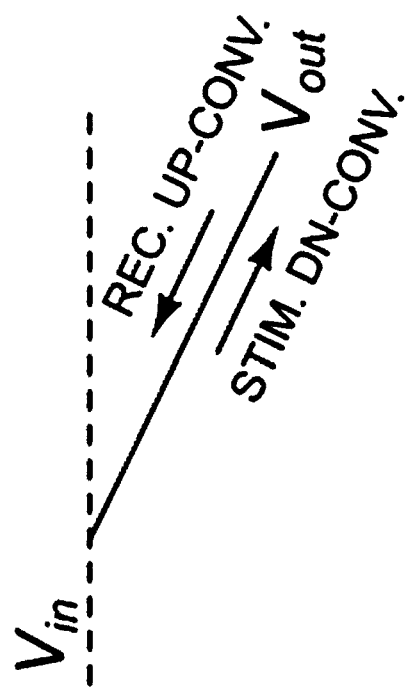

The adaptive voltage stimulator described above implemented two modes of operation: stimulating down-conversion and recycling up-conversion. These two modes provide for bidirectional current flow. However, since the electrode voltage should be less than the DC power supply voltage $V_{DD}$, a midrail voltage $V_{mid}$, was used. It is possible to create a single adaptive voltage stimulator capable of four modes of operation: stimulating down-conversion, recycling up-conversion, stimulating up-conversion, and recycling down-conversion. If all four modes are available, then bidirectional current flow is possible without the need for a midrail voltage because the adaptive voltage stimulator can create voltages both above and below $V_{DD}$ and conductor current in either direction. In this configuration, $V_{mid}$ is unnecessary because the electrode baseline potential can be set to $V_{DD}$. FIGS. 22a and 22b show the ideal range output voltages and flow of power for the two-mode adaptive voltage stimulator (FIG. 22a) and the four-mode adaptive voltage stimulator (FIG. 22b).

FIGS. 23a-23c show both two-mode adaptive voltage stimulators, and a four-mode adaptive voltage stimulator. To create the four-mode adaptive voltage stimulator, the standard adaptive voltage stimulator having two modes, stimulating down-conversion and recycling up-conversion, shown in FIG. 23a is duplicated in a mirror image, as shown in FIG. 23b. FIG. 23b, therefore shows a second adaptive voltage stimulator with two modes, stimulating up-conversion and recycling down-conversion. Combining the stimulators of FIG. 23a and FIG. 23b, the complete four-mode adaptive voltage stimulator is generated, as shown in FIG. 23c. The capacitors $C_{in}$ and $C_{out}$ have the same function as they did in the original two-mode adaptive voltage stimulator. To operate this adaptive voltage stimulator, a table showing proper positions of the switches $M_{p1}$, $M_{n1}$, $M_{p2}$, and $M_{n2}$ for the $D_1$ and $D_2$ phases of pulse operation is given in Table 3, below.

TABLE 3

| | $D_1$ | | | | $D_2$ | | | |
|---|---|---|---|---|---|---|---|---|
| Mode | $M_{p1}$ | $M_{n1}$ | $M_{p2}$ | $M_{n2}$ | $M_{p1}$ | $M_{n1}$ | $M_{p2}$ | $M_{n2}$ |
| Stimulating Down-Conversion | ○ | — | ○ | — | — | ○ | ○ | — |
| Recycling Up-Conversion | — | ○ | ○ | — | ○ | — | ○ | — |
| Stimulating Up-Conversion | ○ | — | — | ○ | ○ | — | ○ | — |
| Recycling Down-Conversion | ○ | — | ○ | — | ○ | — | — | ○ |

In the implementation described above, the inductor of the adaptive voltage stimulator was operated in the discontinuous conduction mode. The adaptive voltage stimulator is designed such that of the 4 μs period between subsequent pulses of the adaptive voltage stimulator, the total combined duration of the pulses $D_1$ and $D_2$ did not exceed 1 μs. Because the inductor current falls to zero at the end of a pulsing cycle, it is possible to reuse the inductor up to 3 additional times, for a total of 4 electrodes in one 4 μs period.

Figure 24:
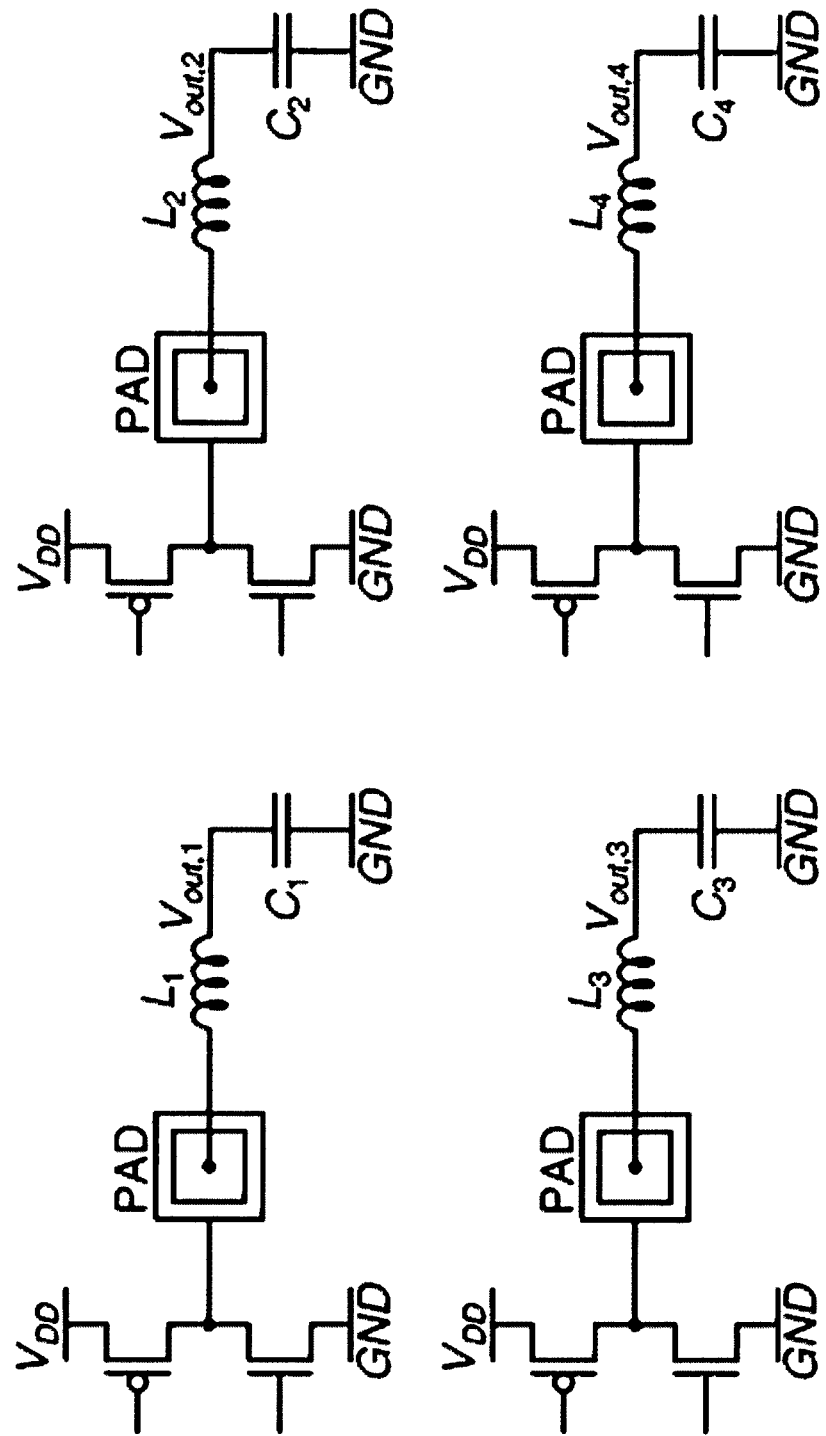
FIG. 24 is a schematic diagram of some of the components of a four channel adaptive voltage stimulator showing four copies of the stimulator circuitry.

FIG. 24 shows a simplified adiabatic stimulator with 4 channels, focusing on just the switches of the adaptive voltage stimulator, the inductor, and output filter capacitor. An individual inductor is provided for each channel, labeled $L_1$-$L_4$. In addition, each channel has its own output filter capacitor, labeled $C_1$-$C_4$. The bonding pads indicated show the connection between on-chip and off-chip components. Individual electrodes are connected to the voltage $V_{out,1}$-$V_{out,4}$.

Figure 25:
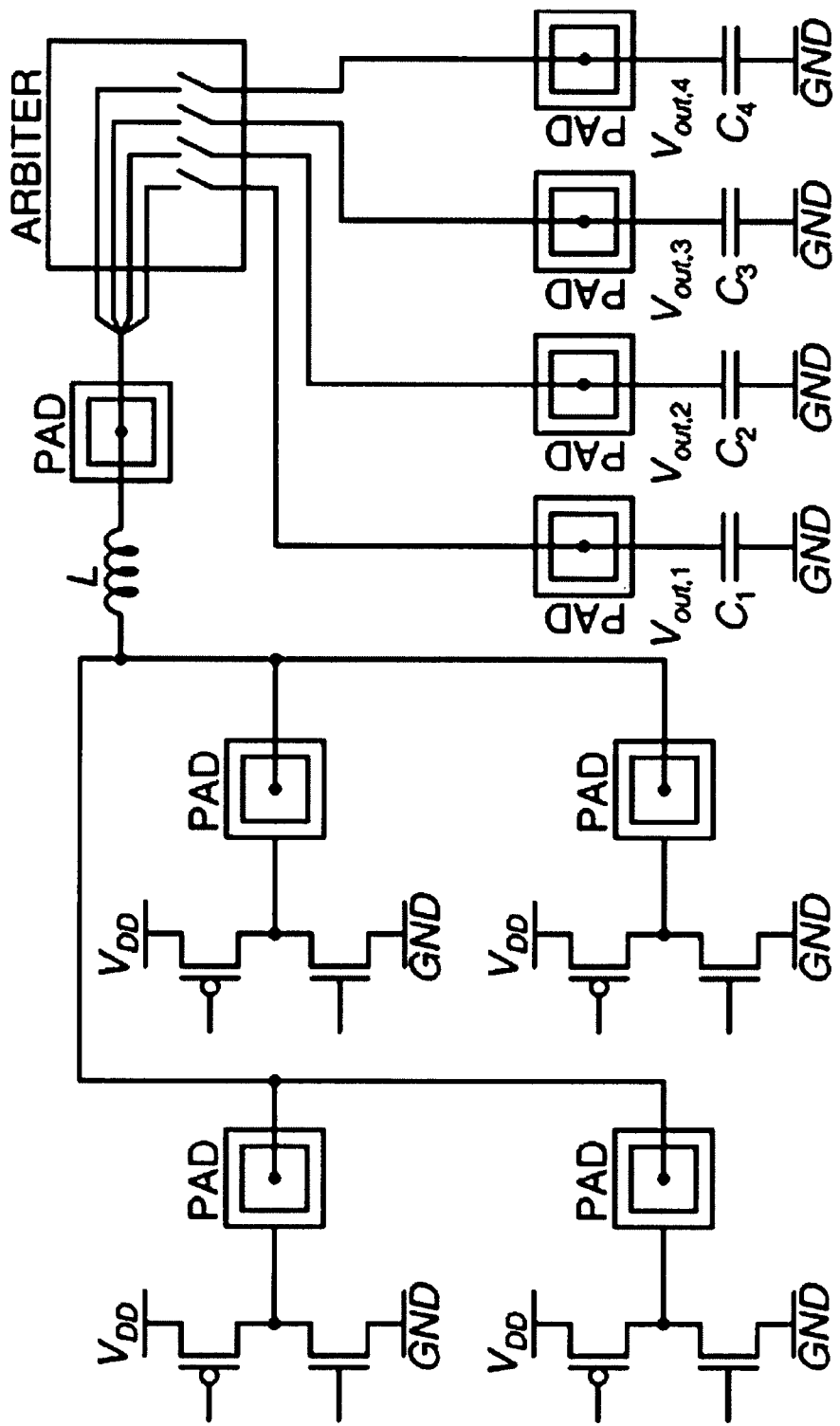
FIG. 25 is a schematic diagram of a simplified adiabatic stimulator with 4 channels utilizing a single inductor that is multiplexed amongst the four channels, where capacitors are used to maintain electrode voltage between pulses of the adaptive voltage stimulator.

Using the discontinuous conduction mode of the inductor and time-share, or multiplexing that inductor amongst four channels, only a single inductor is needed. FIG. 25 shows a simplified adiabatic stimulator with 4 channels utilizing a single inductor that is multiplexed amongst the four channels. In this configuration, four output filter capacitors $C_1$-$C_4$ are still required to maintain the electrode voltage between pulses of the adaptive voltage stimulator. However, the inductor may be zero-current switched by the arbiter between each of the four channels in succession. Thus, only one channel may be pulsing at any given time, but a single inductor may be multiplexed across four channels. In principle, any number of channels is possible.

Figure 26:
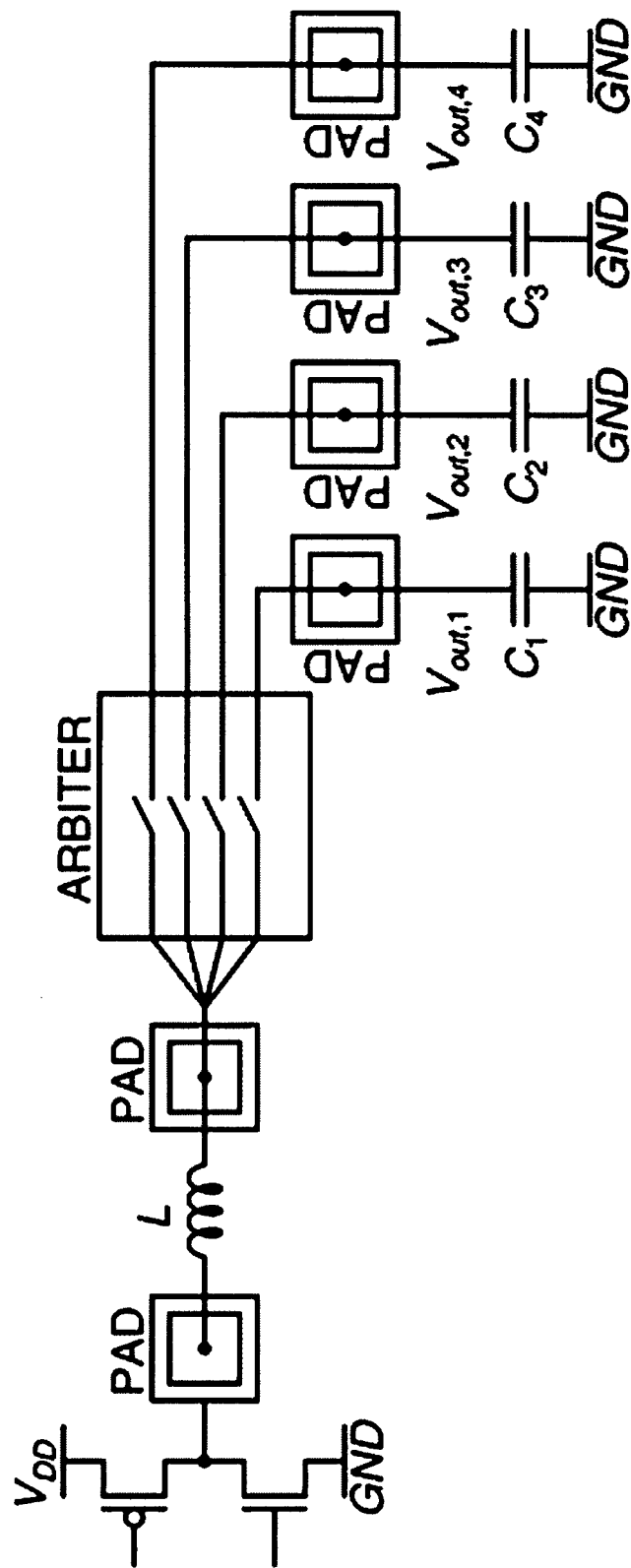
FIG. 26 is a schematic diagram of a simplified adaptive voltage stimulator with four stimulation channels that uses a single inductor multiplexed across four channels.

FIG. 26 is an illustration of another implementation of a four-channel adiabatic stimulator. Because only one stimulator channel may be pulsing at any given time, only a single adaptive voltage stimulator is need for all four channels. Thus, the arbiter zero-current switches the inductor through the four channels at intervals. The capacitors $C_1$-$C_4$ maintain the individual electrode voltages between pulses, and the output voltage $V_{out,1}$-$V_{out,4}$ are connected to each electrode respectively.

Figure 27:
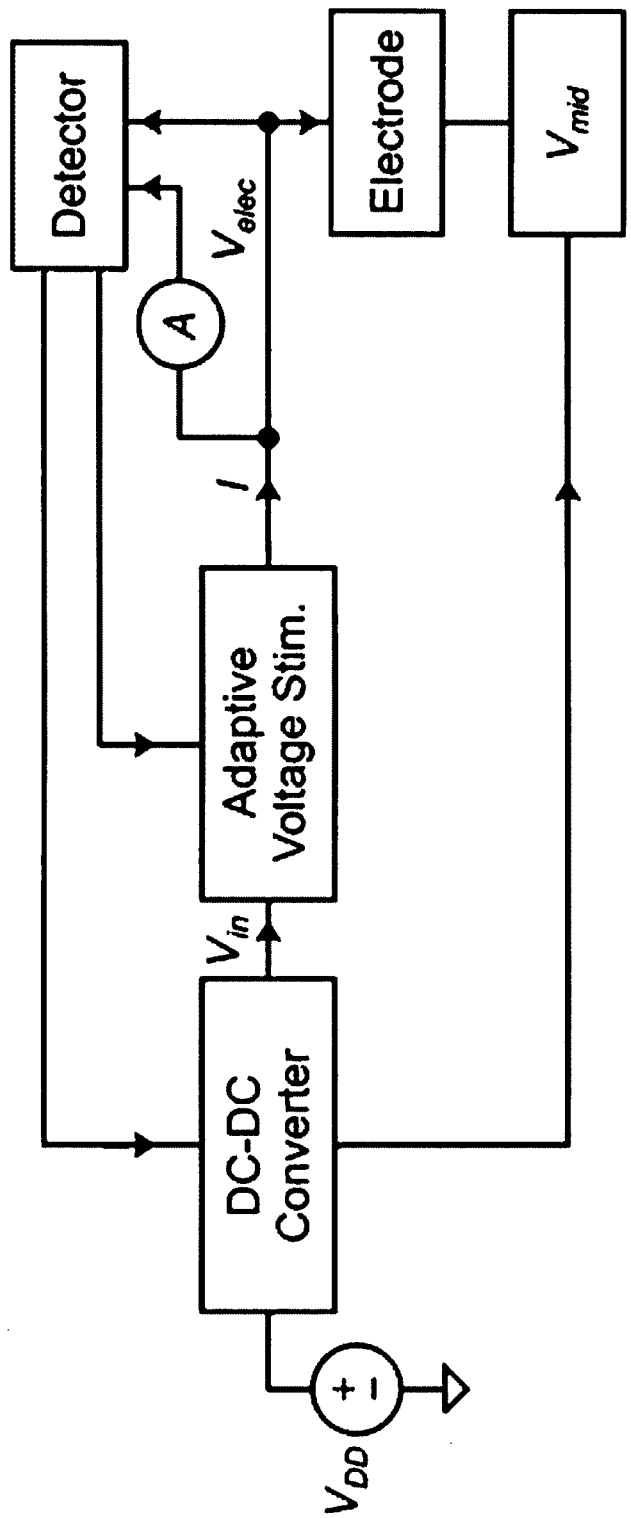
FIG. 27 is a diagram showing some of the functional component of an adaptive class A voltage stimulator.

It is possible to improve the performance of the adaptive voltage stimulator by matching the input voltage of the adaptive voltage stimulator $V_{in}$ to the requirements of the electrode. For example, for a given level of stimulation and a given electrode impedance, there is a particular peak-to-peak deflection of electrode voltage $V_{elec}$. The adaptive voltage stimulator is able to adapt and track the electrode voltage, but also stores energy in $V_{mid}$. If the peak-to-peak electrode voltage is small, most of the energy loss in the adaptive voltage stimulator is due to the shuttling of energy in and out of the $V_{mid}$ voltage reference rather than due to the electrode itself. If the detector as shown in FIG. 27 also reported peak voltage deflections of $V_{elec}$, a true DC-DC converter located at the input to the adaptive voltage stimulator could adjust the $V_{in}$ and $V_{mid}$ higher or lower depending on the requirements of the electrode, thus further saving energy.

The present system provides an integrated-circuit adiabatic electrode stimulator that uses an adaptive voltage stimulator as a variable voltage source to efficiently drive an electrode with positive or negative current. The stimulator also monitors the current flow into or out of the electrode based upon a shunt current sensing technique, and adjusts the voltage output of the adaptive voltage stimulator to maintain a constant current as selected by the user. This shunt technique operates on micropower and draws little current from the electrode, avoiding the need for series current sense resistors or dissipative current limiters. The present disclosure has demonstrated reductions in energy usage of at least 2-3× over conventional stimulators based on current sources.

The current sensing circuit makes the current output independent of the electrode impedance, a problem which routinely stymies other voltage-based stimulators due to highly variable electrode impedances. Because this technique is general, it can be used to drive many impedances, including LEDs for optical based stimulators. When used in implantable medical devices, these energy reductions offered by the present stimulator can be used to decrease the size of implanted batteries or coils, thereby reducing device size, increasing battery life time, reducing device costs, reducing heat dissipation, and increasing the quality of life of the patients. The stimulator may be useful in cardiac, neural, muscular, cochlear, retinal, and other biomedical implants.

The present invention has been described in terms of one or more embodiments, and it should be appreciated that many equivalents, alternatives, variations, and modifications, aside from those expressly stated, are possible and within the scope of the invention.

The invention claimed is:

1. A medical device configured to be connected to a subject and deliver an electrical stimulation to tissue of the subject, the medical device comprising:
    a direct current (DC) voltage power source;
    an electrode configured to deliver the electrical stimulation to the tissue of the subject;
    a sensor circuit connected to the electrode and the DC voltage power source, the sensor circuit being configured to:
        measure a power characteristic of the electrode,
        compare the measured power characteristic of the electrode to a desired power characteristic,
        determine a current mode of operation of the medical device, the current mode of operation being a stimulating down-conversion mode or a recycling up-conversion mode, and
        based upon the comparison of the measured power characteristic of the electrode and the desired power characteristic, at least one of increment and decrement a counter;
    a pulse generator configured to use the counter and the current mode of operation of the medical device to generate a timing sequence; and
    a stimulator core including at least two switches configured to be controlled by the timing sequence to at least one of deliver energy from the DC voltage power source to the electrode to stimulate the tissue and recover energy from the electrode.

2. The medical device of claim 1, wherein delivering energy to the electrode comprises:
    supplying energy to an inductor connected to the electrode stimulator; and
    discharging energy from the inductor into the electrode.

3. The medical device of claim 2, including an arbiter connected to the inductor, the arbiter being configured to switch the inductor between a plurality of connected electrodes to supply energy to, or recover energy from, each one of the plurality of electrodes.

4. The medical device of claim 1, wherein the sensor circuit comprises a current sensor configured to measure a current flow through the electrode.

5. The medical device of claim 4, wherein the sensor circuit is configured in a shunt sensor arrangement.

6. An electrode stimulator configured to connect to a medical device having at least one electrode configured to deliver an electrical stimulation to tissue of a subject having the medical device, the electrode stimulator comprising:
    a sensor circuit configured to be coupled to the at least one electrode of the medical device to measure a power characteristic of the at least one electrode; and
    a control circuit configured to:
        determine a current mode of operation, the current mode of operation being a stimulating down-conversion mode or a recycling up-conversion mode,
        compare the measured power characteristic of the at least one electrode to a desired power characteristic,
        based upon the comparison of the measured power characteristic of the at least one electrode and the desired power characteristic and the current mode of operation, generate a timing sequence, and
        use the timing sequence to stimulate the electrode according to a first operational mode or a second operational mode of the electrode stimulator to at least one of deliver energy from a DC voltage source to the at least one electrode to stimulate the tissue and recover energy from the electrode.

7. The electrode stimulator of claim 6, wherein delivering energy to the at least one electrode comprises:
    supplying energy to an inductor connected to the electrode stimulator; and
    discharging energy from the inductor into the at least one electrode.

8. The electrode stimulator of claim 7, including an arbiter connected to the inductor, the arbiter being configured to switch the inductor between a plurality of connected electrodes to supply energy to, or recover energy from, each one of the plurality of electrodes.

9. The electrode stimulator of claim 6, wherein the sensor circuit comprises a current sensor configured to measure a current flow through the at least one electrode.

10. The electrode stimulator of claim 9, wherein the sensor circuit is configured in a shunt sensor arrangement.

* * * * *

UNITED STATES PATENT AND TRADEMARK OFFICE
CERTIFICATE OF CORRECTION

PATENT NO. : 8,700,144 B2
APPLICATION NO. : 13/096670
DATED : April 15, 2014
INVENTOR(S) : Scott K. Arfin and Rahul Sarpeshkar It is certified that error appears in the above-identified patent and that said Letters Patent is hereby corrected as shown below:

In the Specification:

Column 26, line 5 "a" should be -- approximately --

Signed and Sealed this
Fifteenth Day of July, 2014

Michelle K. Lee
*Deputy Director of the United States Patent and Trademark Office*